United States Patent
Hori et al.

(10) Patent No.: US 10,267,759 B2
(45) Date of Patent: Apr. 23, 2019

(54) METHOD OF DETECTING TEST SUBSTANCE

(71) Applicant: SYSMEX CORPORATION, Kobe-shi, Hyogo (JP)

(72) Inventors: Nobuyasu Hori, Kobe (JP); Yuichi Yasuda, Kobe (JP); Hiroya Kirimura, Kobe (JP); Yuzuru Takamura, Kobe (JP); Miyuki Chikae, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 453 days.

(21) Appl. No.: 14/923,515

(22) Filed: Oct. 27, 2015

(65) Prior Publication Data

US 2016/0116428 A1    Apr. 28, 2016

(30) Foreign Application Priority Data

Oct. 28, 2014   (JP) ................. 2014-219449

(51) Int. Cl.
*G01N 27/327* (2006.01)
*G01N 27/74* (2006.01)
*G01N 33/543* (2006.01)

(52) U.S. Cl.
CPC ..... *G01N 27/3278* (2013.01); *G01N 27/3277* (2013.01); *G01N 27/745* (2013.01); *G01N 33/5438* (2013.01); *G01N 33/54313* (2013.01)

(58) Field of Classification Search
CPC ............. G01N 27/3278; G01N 27/745; G01N 27/3277; G01N 33/5438; G01N 33/54313
See application file for complete search history.

(56) References Cited

U.S. PATENT DOCUMENTS

| | | | |
|---|---|---|---|
| 2008/0185295 A1* | 8/2008 | Briman | G01N 33/5438 205/777.5 |
| 2009/0092965 A1* | 4/2009 | Weiss | G01N 27/327 435/5 |

(Continued)

FOREIGN PATENT DOCUMENTS

| | | |
|---|---|---|
| CN | 104020198 A | 9/2014 |
| JP | 4915740 B2 | 4/2012 |
| JP | 5187759 B2 | 4/2013 |

OTHER PUBLICATIONS

H. Huang, et al. "Application of electrochemical impedance spectrscopy for monitoring allergen-antibody reactions using gold nanoparticle-based biomolecular immobilization method", Analytical Biochemistry, vol. 356, p. 208-214. (Year: 2006).*

(Continued)

*Primary Examiner* — J. Christopher Ball
(74) *Attorney, Agent, or Firm* — Sughrue Mion, PLLC

(57) ABSTRACT

Disclosed is a method of detecting a test substance contained in a sample using a working electrode and a counter electrode. The method comprises (A) forming a complex on the working electrode, the complex comprising the test substance and a metal particle; (B) washing the working electrode; (C) adding a measurement solution to the working electrode and measuring a current, voltage or electric charge from the metal on the working electrode in the measurement solution by electrochemical measurement; and (D) detecting the test substance in the sample based on a measurement result obtained in the step (C). In the method, the step (B) comprises washing the working electrode using a measurement solution having the same composition as the composition of the measurement solution used in the step (C). In the method, pH of the measurement solution is set, based on zeta potentials of the metal particle and the working electrode, to pH in which no electrostatic interaction occurs between the metal particle and the working electrode or pH in which an electrostatic repulsive force occurs between the metal particle and the working electrode.

17 Claims, 12 Drawing Sheets

(56) References Cited

U.S. PATENT DOCUMENTS

2009/0159458 A1    6/2009  Tamiya et al.
2011/0287977 A1*  11/2011  Cai .................. G01N 33/54346
                                                              506/13

OTHER PUBLICATIONS

M. Ozsoz, et al. "Electrochemical genosensor based on colloidal gold nanoparticles for the detection of Factor V Leiden mutation using disposable pencil graphite electrodes", Analytical Chemistry, 75(9): p. 2181-2187, May 1, 2003.*

Koutarou Idegami, et al., "Gold Nanoparticle-Based Redox Signal Enhancement for Sensitive Detection of Human Chorionic Gonadotropin Hormone", Electroanalysis, 2008, pp. 14-21, vol. 20, No. 1.

Miyuki Chikae, et al., "Highly Sensitive Method for Electrochemical Detection of Silver Nanoparticle Labels in Metalloimmunoassay with Preoxidation/Reduction Signal Enhancement", Electrochemistry, 2010, pp. 748-753, vol. 78, No. 9.

Jung Jin Park et al., "Langmuir Adsorption Study of the Interaction of CdSe/ZnS Quantum Dots with Model Substrates: Influence of Substrate Surface Chemistry and pH", Langmuir, 2009, vol. 25, No. 1, pp. 443-450(9 pgs. total).

* cited by examiner

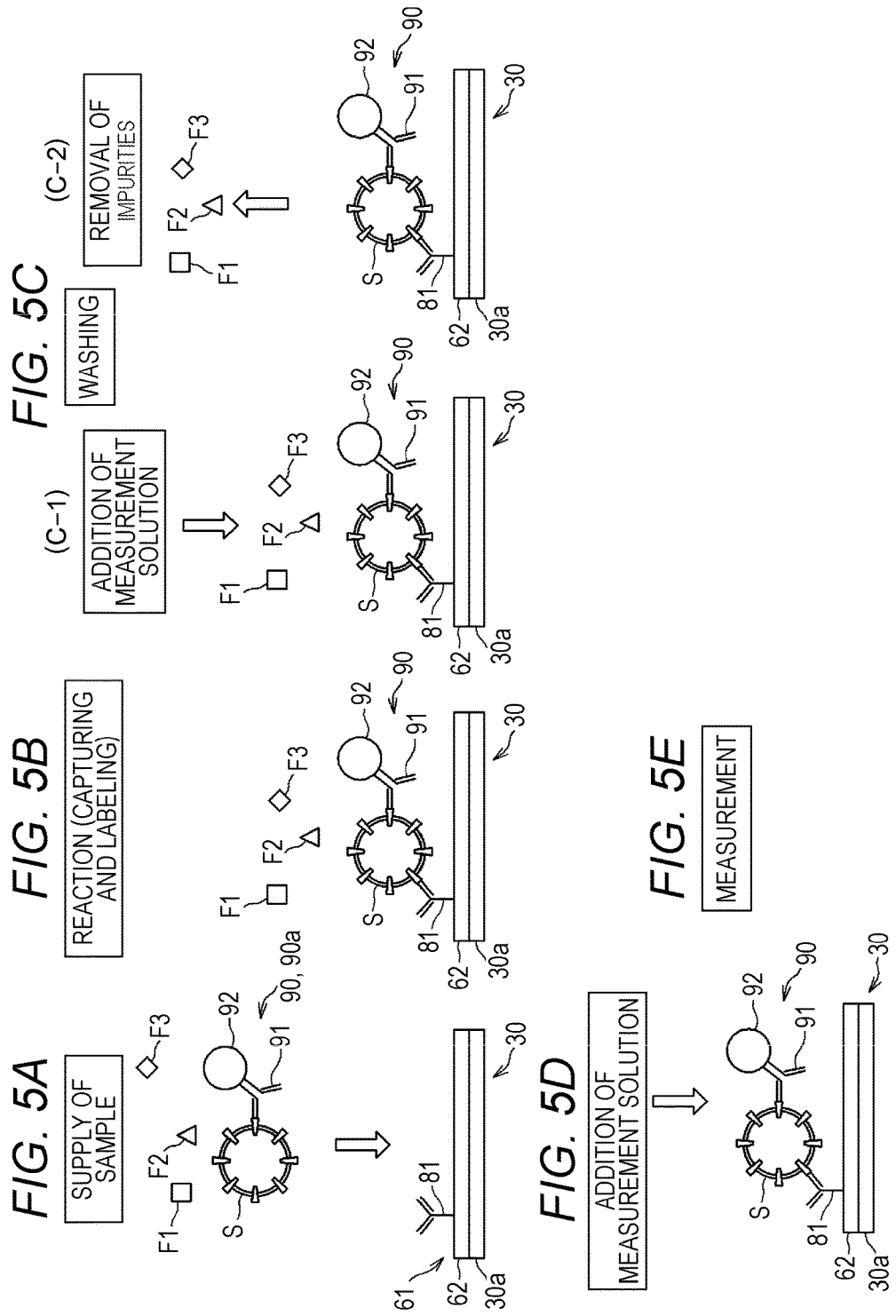

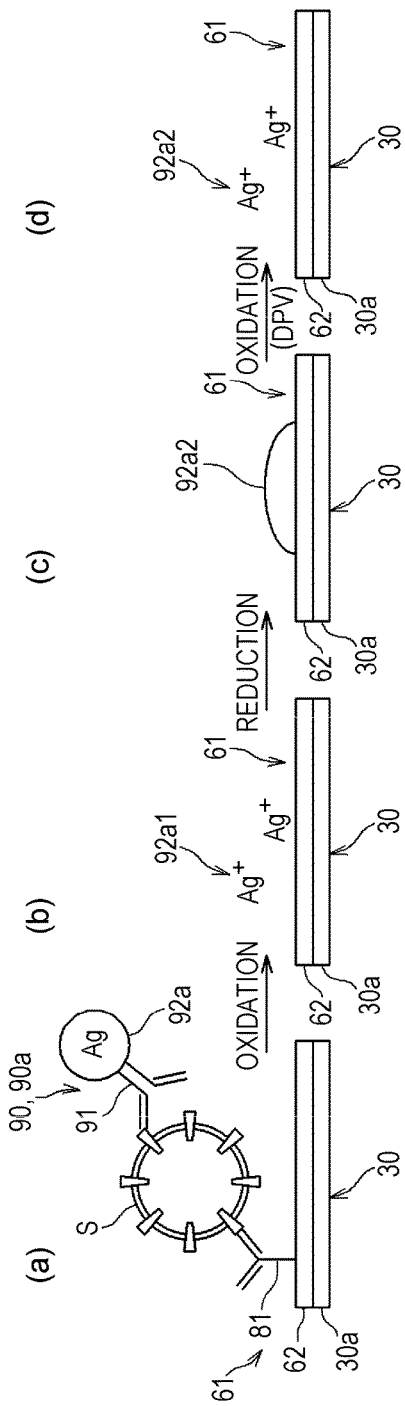
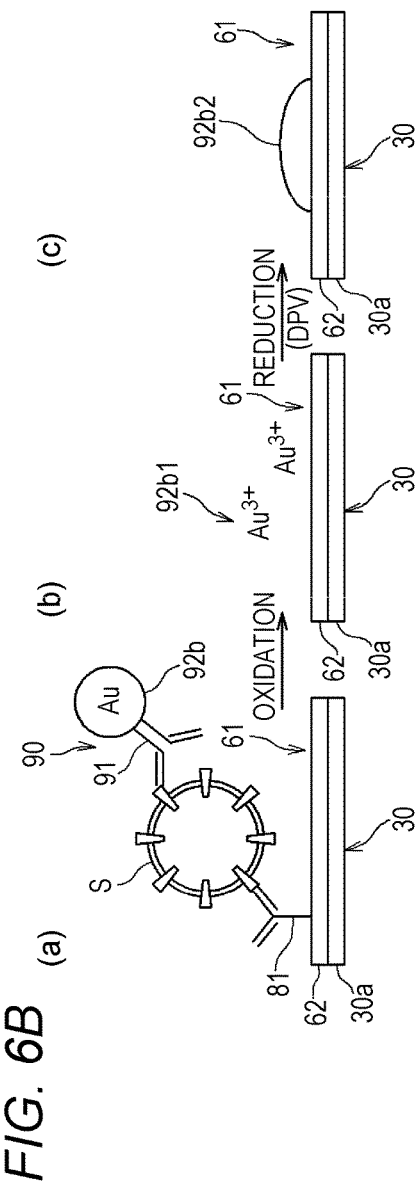
FIG. 6A
FIG. 6B

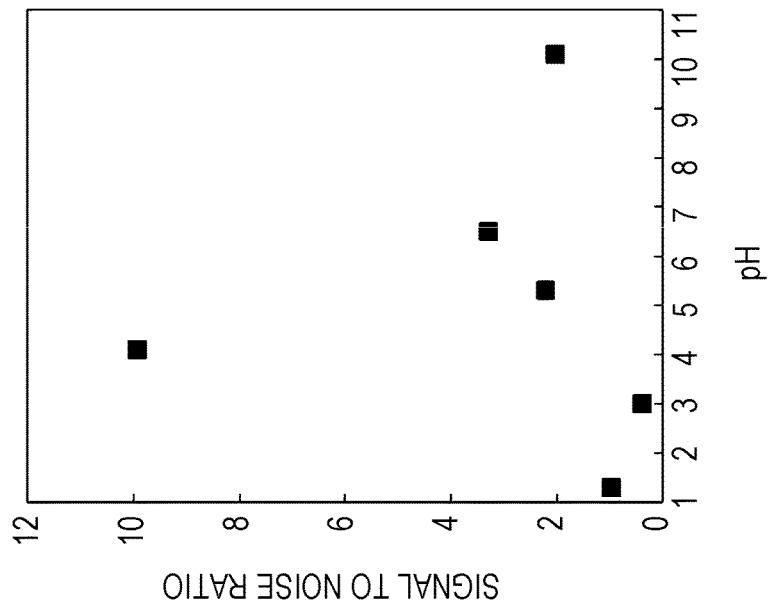
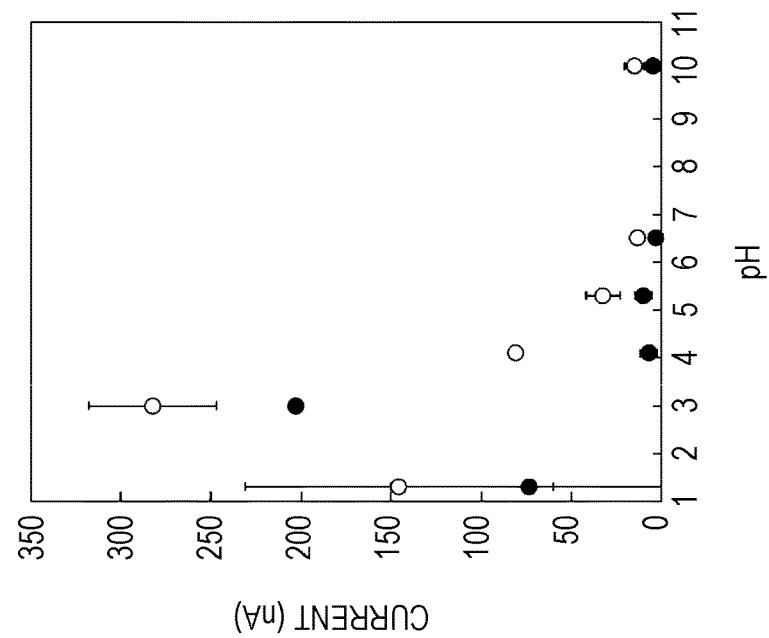

METHOD OF DETECTING TEST SUBSTANCE

CROSS REFERENCE TO RELATED APPLICATIONS

This application claims priority from prior Japanese Patent Application No. 2014-219449, filed on Oct. 28, 2014, entitled "METHOD OF DETECTING TEST SUBSTANCE", the entire contents of which are incorporated herein by reference.

TECHNICAL FIELD

The present invention relates to a method of detecting a test substance. More particularly, the invention relates to a method of detecting a test substance, which is useful for detecting, quantifying, etc. a test substance as a bio-related substance contained in a sample.

BACKGROUND

As a method of detecting a test substance (i.e., a bio-related substance contained in a sample), a known method is, for example, a method comprising: using a test substance, a specific binding substance which specifically recognizes the test substance, and metal particles; capturing in a neighborhood of a surface of a working electrode the metal particles in an amount corresponding to an amount of the test substance by using biological interactions (e.g., antigen-antibody reaction); and electrochemically measuring the amount of the captured metal particles (for example, refer to U. S. Patent Application Publication No. 2009/159458, Japanese Patent No. 4915740, Koutarou Idegami et al., "Gold Nanoparticle-Based Redox Signal Enhancement for Sensitive Detection of Human Chorionic Gonadotropin Hormone", Electroanalysis, vol. 20, pp. 14-21, published on Sep. 27, 2007, and Miyuki Chikae et al., "Highly Sensitive Method for Electrochemical Detection of Silver Nanoparticle Labels in Metalloimmunoassay with Preoxidation/Reduction Signal Enhancement", Electrochemistry, vol. 78, pp. 748-753, published in 2010, all of which are incorporated herein by reference).

U. S. Patent Application Publication No. 2009/159458 and Koutarou Idegami et al. disclose a method of detecting a test substance, comprising the steps of: capturing in a neighborhood of a surface of a working electrode gold particles in an amount corresponding to an amount of the test substance by using biological interactions; electrochemically oxidizing the captured gold particles to be eluted; and measuring a current induced by reducing the eluted gold ions. Japanese Patent No. 4915740 or Miyuki Chikae et al. describes a method of detecting a test substance, comprising the steps of: capturing in a neighborhood of a surface of a working electrode silver particles in an amount corresponding to an amount of the test substance by using biological interactions; electrochemically oxidizing the captured silver particles to be eluted; reducing the eluted silver ions to deposit the silver on the surface of the working electrode; and measuring a current induced by electrochemically oxidizing the deposited silver.

SUMMARY OF THE INVENTION

The scope of the present invention is defined solely by the appended claims, and is not affected to any degree by the statements within this summary.

Provided is a method of detecting a test substance contained in a sample using a working electrode and a counter electrode. The method comprises (A) forming a complex on the working electrode, the complex comprising the test substance and a metal particle; (B) washing the working electrode; (C) adding a measurement solution to the working electrode and measuring a current, voltage or electric charge from the metal on the working electrode in the measurement solution by electrochemical measurement; and (D) detecting the test substance in the sample based on a measurement result obtained in the step (C). In the method, the step (B) comprises washing the working electrode using a measurement solution having the same composition as the composition of the measurement solution used in the step (C). In the method, pH of the measurement solution is set, based on zeta potentials of the metal particle and the working electrode, to pH in which no electrostatic interaction occurs between the metal particle and the working electrode or pH in which an electrostatic repulsive force occurs between the metal particle and the working electrode.

In another aspect, provided is a method of detecting a test substance contained in a sample using a working electrode and a counter electrode. The method comprises: (A) forming a complex on the working electrode, the complex comprising the test substance and a metal particle; (B) washing the working electrode; (C) adding a measurement solution to the working electrode and measuring a current, voltage or electric charge from the metal on the working electrode in the measurement solution by electrochemical measurement; and (D) detecting the test substance in the sample based on a measurement result obtained in the step (C). In the method, the step (B) comprises washing the working electrode using a measurement solution having the same composition as the composition of the measurement solution used in the step (C). In the method, the measurement solution has a pH of 3.5 or more.

In another aspect, provided is a method of detecting a test substance contained in a sample using a working electrode and a counter electrode. The method comprises: (A) forming a complex on the working electrode, the complex comprising the test substance and a metal particle; (B) adding a measurement solution to the working electrode and removing the measurement solution to remove an impurity; (C) adding a measurement solution to the working electrode and measuring a current, voltage or electric charge from the metal on the working electrode in the measurement solution by electrochemical measurement; and (D) detecting the test substance in the sample based on a measurement result obtained in the step (C). In the method, the measurement solution used in the step (B) has the same composition as the composition of the measurement solution used in the step (C). In the method, the measurement solution has a pH of 3.5 or more. In the method, the working electrode comprises carbon.

BRIEF DESCRIPTION OF THE DRAWINGS

FIGS. 5A to 5E are explanatory views of the steps showing procedures of the method of detecting a test substance according to one embodiment of the present invention;

FIGS. 6A and 6B are explanatory views of the steps showing procedures in the measurement step of the method of detecting a test substance according to one embodiment of the present invention;

FIG. 8A is a graph showing the results obtained by examining the relationship between the current from silver particles in a labeled complex which have been formed in a neighborhood of a surface of a working electrode and the pH of a measurement solution in Test Example 2, and FIG. 8B is a graph showing the results obtained by examining the relationship between the signal to noise ratio when measuring the current from silver particles in the labeled complex which have been gathered in a neighborhood of the surface of the working electrode and the pH of the measurement solution in Test Example 2;

DETAILED DESCRIPTION OF THE PREFERRED EMBODIMENTS

[Configuration of Detector]

First, an example of a detector to be used in a method of detecting a test substance according to one embodiment will be described with reference to the attached drawings.

Figure 1:
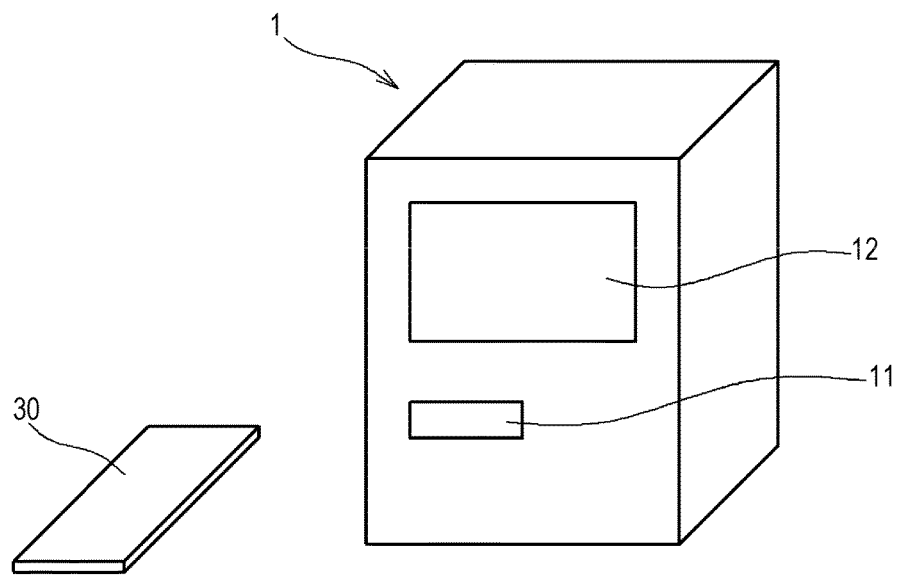
FIG. 1 is a perspective view showing a detector to be used for a method of detecting a test substance according to one embodiment of the present invention.

In FIG. 1, a detector 1 includes a substrate receiving unit 11 into which an electrode substrate 30 is inserted and a display 12 which displays the detection results.

Figure 2:
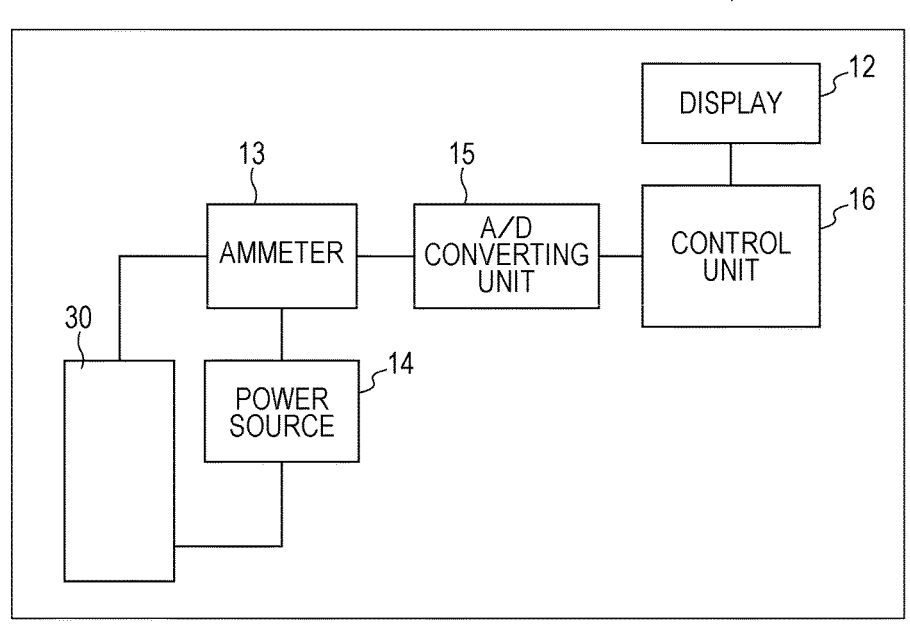
FIG. 2 is a block diagram showing a configuration of the detector shown in FIG. 1.

As shown in FIG. 2, the detector 1 includes the display 12, an ammeter 13, a power source 14, an A/D converting unit 15, and a control unit 16.

The ammeter 13 measures a current induced by oxidizing metal particles or reducing metal ions as a labeling substance. The power source 14 applies a predetermined potential to an electrode formed on the electrode substrate 30. The A/D converting unit 15 digitally converts the current values measured by the ammeter 13. The control unit 16 is configured to include Central Processing Unit (CPU), Read Only Memory (ROM), Random Access Memory (RAM), and the like. The control unit 16 controls the operation of the display 12, the ammeter 13, and the power source 14. The control unit 16 may be one that estimates the amount of the labeling substance from the current value which has been digitally converted by the A/D converting unit 15 based on a calibration curve indicating a relationship between a current value created in advance and the amount of the labeling substance and calculates the amount of the test substance. The display 12 displays information such as the amount of the test substance which has been estimated by the control unit 16.

[Configuration of Electrode Substrate]

The configuration of the electrode substrate 30 to be used for the method of detecting a test substance according to one embodiment will be described.

Figure 3:
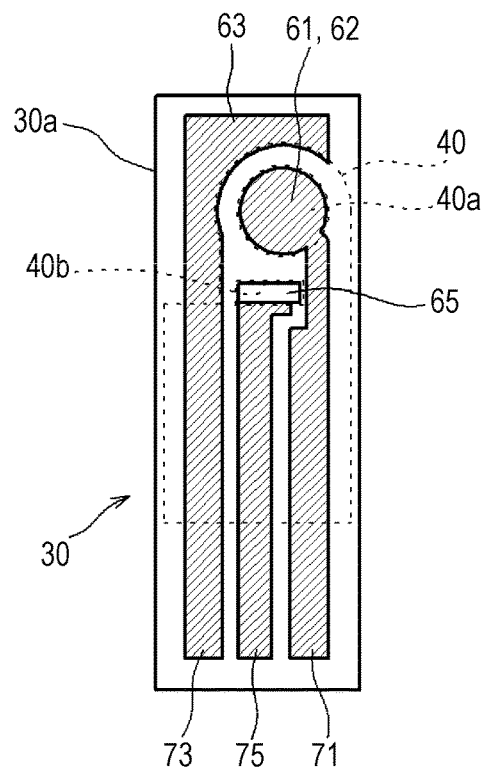
FIG. 3 is a front view showing an electrode substrate to be used for the method of detecting a test substance according to one embodiment of the present invention.
Figure 4:
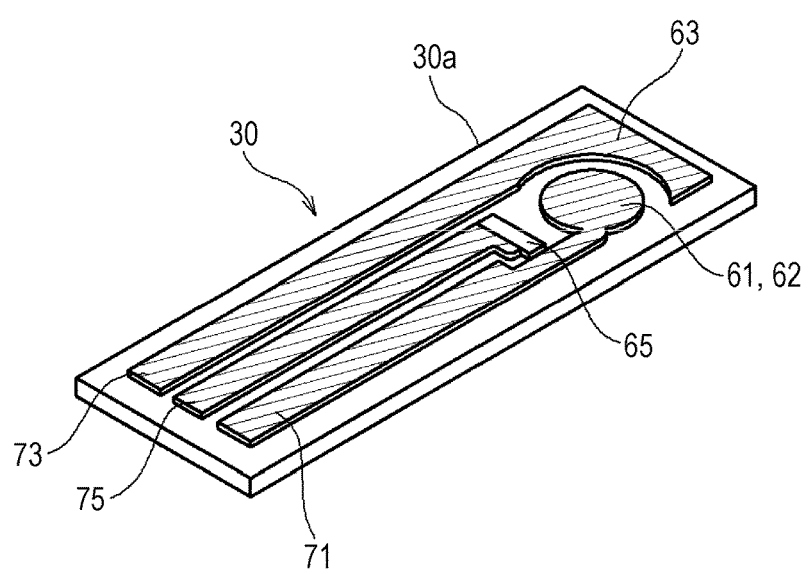
FIG. 4 is a perspective view showing a configuration of a main part of the electrode substrate shown in FIG. 3.

As shown in FIGS. 3 and 4, the electrode substrate 30 includes a substrate body 30a, a working electrode 61, a counter electrode 63, and a reference electrode 65. The working electrode 61 and an electrode lead 71 connected to the working electrode 61, the counter electrode 63 and an electrode lead 73 connected to the counter electrode 63, and the reference electrode 65 and an electrode lead 75 connected to the reference electrode 65 are formed on a surface of the substrate body 30a. A part of each of the electrode leads 71, 73, and 75 is covered with a leakage preventing member 40 which prevents the electrode leads 71, 73, and 75 from being brought into contact with the leaked measurement solution. The leakage preventing member 40 has hole portions 40a and 40b formed therein so that the working electrode 61 and the reference electrode 65 are exposed.

The working electrode 61 is disposed at one side portion [the upper side of FIG. 3] of the substrate body 30a. The electrode lead 71 is extended from the working electrode 61 to the other side portion of the substrate body 30a [the lower side of FIG. 3]. The counter electrode 63 is disposed outside of the working electrode 61 [the upper side of the working electrode 61 in FIG. 3] on the substrate body 30*a*. The electrode lead 73 is bypassed the working electrode 61 and the reference electrode 65 and extended from the counter electrode 63 to the other side portion of the substrate body 30*a* [the lower side of FIG. 3]. The reference electrode 65 is disposed at the position of facing the counter electrode 63 across the working electrode 61. The electrode lead 75 is extended from the reference electrode 65 to the other side portion of the substrate body 30*a* [the lower side of FIG. 3]. The electrode lead 71 connected to the working electrode 61, the electrode lead 73 connected to the counter electrode 63, and the electrode lead 75 connected to the reference electrode 65 are disposed so as to be parallel to one another at the other side portion of the substrate body 30*a* (the lower side of FIG. 3).

In the embodiment, the substrate body 30*a* is formed into a rectangular shape. There is no particular limitation as to the shape of the substrate body 30*a* and it may be polygonal, discoid, or the like.

Examples of the material for forming the substrate body 30*a* include plastics such as polyethylene terephthalate, polyimide resin, and glass epoxy; and inorganic materials such as glass and metal. However, the present embodiment is not limited only to the examples. Since the thickness of the substrate body 30*a* varies depending on the purpose of the method of detecting a test substance, etc., it is desirable to appropriately determine the thickness of the substrate body 30*a* in accordance with the purpose of the method of detecting a test substance, etc.

The working electrode 61 is configured to include a working electrode body 62 and a capturing substance immobilized on a surface of the working electrode body 62. The working electrode body 62 is formed of a conductive thin film. The conductive thin film is mainly formed of a conductive material. Examples of the conductive material include carbon materials such as graphite, glassy carbon, pyrolytic graphite, carbon paste, carbon fiber, carbon nanotube, and graphene; metal materials such as gold and platinum; and oxide semiconductors such as tin-doped indium oxide (ITO) and fluorine-doped tin oxide (FTO). However, the present embodiment is not limited only to the examples. The working electrode body 62 may be formed of a composite base material in which a conductive layer made of a conductive material is formed on a surface of a nonconductive base material made of a nonconductive substance such as glass or plastic. Since the thickness of the thin film forming the working electrode body 62 varies depending on the purpose of the method of detecting a test substance, etc., it is desirable to appropriately determine the thickness of the thin film in accordance with the purpose of the method of detecting a test substance, etc. A capturing substance is immobilized on the surface of the working electrode body 62. The capturing substance is a substance for capturing a test substance. Since the capturing substance varies depending on the type of the test substance, etc., it is desirable to appropriately determine the capturing substance in accordance with the type of the test substance, etc. Examples of the capturing substance include nucleic acids, proteins, peptides, sugar chains, antibodies, and nanostructures with specific recognition ability. However, the present embodiment is not limited only to the examples. The amount of the capturing substance per unit area to be immobilized on the working electrode body 62 varies depending on the type of the test substance, the type of the capturing substance, the purpose of the method of detecting a test substance, etc. Accordingly, it is desirable to appropriately determine the amount of the capturing substance in accordance with the type of the test substance, the type of the capturing substance, the purpose of the method of detecting a test substance, etc. The amount of the capturing substance per unit area to be immobilized on the working electrode body 62 may be a sufficient amount to capture the test substance.

The counter electrode 63 is formed of a conductive thin film. The conductive thin film is mainly formed of a conductive material. Since the thickness of the thin film forming the counter electrode 63 varies depending on the purpose of the method of detecting a test substance, etc., it is desirable to appropriately determine the thickness of the thin film in accordance with the purpose of the method of detecting a test substance, etc.

The reference electrode 65 is formed of a thin film made of a conductive material. Examples of the conductive material include metals such as gold, silver, copper, carbon, platinum, palladium, chromium, aluminum, and nickel; an alloy containing at least one of those metals; and metal halides such as chlorides of the metals. However, the present embodiment is not limited only to the examples. Specific examples of the reference electrode include a silver-silver chloride electrode and a calomel electrode using mercury and mercury chloride. However, the present embodiment is not limited only to the examples.

Since the thickness of the thin film forming the reference electrode 65 varies depending on the purpose of the method of detecting a test substance, etc., it is desirable to appropriately determine the thickness of the thin film in accordance with the purpose of the method of detecting a test substance, etc. Although the reference electrode 65 is provided in the present embodiment, it is not necessarily to form the reference electrode 65. Depending on the type of the conductive material used for the counter electrode 63, the thickness of the counter electrode 63, etc., when a small current (e.g., 1 µA or less) to be less affected by the voltage drop influences is measured, the counter electrode 63 may serve as the reference electrode 65. When measuring a large current, it is preferable to form the reference electrode 65 from the viewpoint of suppressing voltage drop influences and stabilizing a voltage to be applied to the working electrode 61.

[Procedures of Method of Detecting Test Substance]

Subsequently, the procedures of the method of detecting a test substance according to one embodiment, etc. will be described in detail. The method of detecting a test substance according to one embodiment is a method of detecting a test substance contained in a sample using a working electrode and a counter electrode, the method comprising:

(A) forming a complex that contains the test substance contained in the sample and a metal particle on the working electrode;

(B) washing the working electrode;

(C) adding a measurement solution to the working electrode and measuring a current, voltage or electric charge from the metal particle contained in the complex on the working electrode in the measurement solution by electrochemical measurement; and (D) detecting the test substance in the sample based on measurement results obtained in the step (C), wherein the step (B) includes washing the working electrode using a measurement solution having the same composition as the composition of the measurement solution used in the step (C), and the measurement solution is a solution whose pH is set to a pH in which no electrostatic interaction occurs between the metal particle and the working electrode or a pH in which an electrostatic repulsive force occurs between the metal particle and the working electrode, based on zeta potentials of the metal particle and the working electrode.

Hereinafter, the method of detecting a test substance will also be referred to as "detection method". The term "detecting a test substance" used herein is a concept comprising the steps of: quantifying a test substance by using the number of molecules, mass, concentration, etc. of the test substance as indices; semi-quantifying the test substance such as "highly positive (++)", "weakly positive (+)" or "negative (−)"; and qualitatively determining the presence of the test substance.

Conventionally, when a test substance contained in a sample is detected using a metal particle as a labeling substance, a working electrode, and a counter electrode, nonspecific substances which are present near the surface of the working electrode and cause the noise (e.g., impurities in the sample or unreacted metal particles) are removed by washing with a washing dedicated liquid in order to reduce the noise. However, in this process, the residual of the washing dedicated liquid, the strength of washing, or the like leads to variations in the accuracy of the detection of the test substance. In addition, the washing dedicated liquid is not sufficiently removed from the working electrode or the like before measurement and remains, which may cause an adverse effect on the measurement of the test substance. Consequently, it is necessary to remove the washing dedicated liquid on the working electrode.

Here, an "impurity" means a substance other than the test substance contained in the sample.

On the other hand, since a solution capable of being used as a washing liquid or a measurement solution is used in the present invention, there is no variation in the composition and concentration of the measurement solution to be used when measuring the metal particle by the electrochemical measurement. It is possible to suppress the variations in the accuracy of the detection of the test substance. The number of reagents required to detect the test substance can be reduced. Accordingly, the detection method according to one embodiment allows the operation to be simple. It is possible to prevent mishandling of the reagents by humans, etc. and simplify the detector to be used. In the detection method according to one embodiment, the measurement solution is a solution whose pH is set to a pH in which no electrostatic interaction occurs between the metal particle and the working electrode or a pH in which an electrostatic repulsive force occurs between the metal particle and the working electrode, based on the zeta potentials of the metal particle and the working electrode. Therefore, the detection method according to one embodiment ensures sufficient detection sensitivity without using a washing dedicated liquid having the composition different from that of the measurement solution.

Examples of the test substance include nucleic acids, proteins, peptides, and sugar chains. However, the present embodiment is not limited thereto.

Examples of the biological interaction include an antigen-antibody reaction, a hydrogen bond between nucleic acids, a bond between a nucleic acid and a nucleic acid-binding protein, a bond between a lectin and a sugar chain, and an association between a receptor and a ligand. However, the present embodiment is not limited thereto.

Hereinafter, the procedure of the method of detecting a test substance according to one embodiment will be described based on the accompanying drawings. FIGS. 5A to 5E are explanatory views of the steps showing the procedures of the method of detecting a test substance according to one embodiment. FIGS. 6A to 6B are explanatory views of the steps showing procedures in the measurement step of the method of detecting a test substance according to one embodiment. Hereinafter, the detection method when using the antigen-antibody reaction as the biological interaction will be described as an example. However, the present embodiment is not limited thereto.

A user supplies a measurement sample on the working electrode 61 of the electrode substrate 30 [refer to the step of supplying a sample in FIG. 5A]. Thus, a test substance S in a measurement sample is captured by a capturing substance 81 on the working electrode body 62 formed on the substrate body 30a of the electrode substrate 30. A complex containing the capturing substance 81 on the working electrode body 62 and a labeled complex 90 (complex containing the test substance S and a labeled binding substance 90a) is formed [the reaction in FIG. 5B (refer to the capturing and labeling step)]. At this time, substances other than the test substance S in the measurement sample (impurities F1, F2, F3) are not captured by the capturing substance 81.

In the present embodiment, the measurement sample is prepared by mixing a sample containing the test substance S and the like with the labeled binding substance 90a and binding the test substance S to the labeled binding substance 90a to form the labeled complex 90 prior to the supply to the working electrode 61.

The order of the contact of the capturing substance on the working electrode body, the sample containing the test substance, and the labeled binding substance is not particularly limited to the above process. For example, the labeled complex may be formed on the working electrode body by bringing the capturing substance on the working electrode body into contact with the sample containing the test substance and then bringing the labeled binding substance into contact therewith. The labeled complex may be formed on the working electrode body by adding the labeled binding substance onto the working electrode body and then adding the sample containing the test substance.

The labeled binding substance 90a is configured to include a binding substance 91 bound to the test substance S and a metal particle 92 serving as a labeling substance. The binding substance 91 should be a substance that binds to a position or location different from that of the capturing substance 81 in the test substance S. The binding substance 91 is appropriately selected depending on the type of the test substance S. For example, when the test substance S is a nucleic acid, a nucleic acid probe hybridizing to the nucleic acid, an antibody to the nucleic acid, a protein binding to the nucleic acid or the like may be used as the binding substance 91. When the test substance S is a protein or peptide, an antibody to the protein or peptide may be used as the binding substance 91. Examples of the metal particle 92 include composite particles of metals such as gold particles, silver particles, copper particles, platinum particles, indium particles, gold-silver composite particles, and gold-copper composite particles. However, the present embodiment is not limited thereto. The average particle size of the metal particle 92 is preferably 5 nm or more, more preferably 10 nm or more from the viewpoint of obtaining signals during electrochemical oxidation or reduction. The average particle size is preferably 200 nm or less, more preferably 100 nm or less from the viewpoint of improving the efficiency of capturing the test substance and the efficiency of labeling the test substance. The term "average particle size" used herein means a particle size measured by electron microscope observation, light scattering or the like.

The capturing substance 81 may be appropriately selected depending on the type of the test substance S. When the test substance S is a nucleic acid, a nucleic acid probe hybridizing to the nucleic acid, an antibody to the nucleic acid, a protein binding to the nucleic acid or the like may be used as the capturing substance 81. When the test substance S is a protein or peptide, an antibody to the protein or peptide or the like may be used as the capturing substance 81.

The process of capturing the test substance S by the capturing substance 81 can be performed, for example, under the conditions where the capturing substance 81 is bound to the test substance S. The conditions where the capturing substance 81 is bound to the test substance S can be appropriately selected depending on the type of the test substance S, etc. For example, when the test substance S is a nucleic acid and the capturing substance 81 is a nucleic acid probe hybridizing to the nucleic acid, the process of capturing the test substance S can be performed in the presence of a hybridization buffer. For example, when the test substance S is a nucleic acid, protein or peptide, and the capturing substance 81 is an antibody to the nucleic acid, an antibody to the protein or an antibody to the peptide, the process of capturing the test substance S can be performed by dissolving a specimen as typified by whole blood, plasma, serum, urine, saliva, etc. in a solution suitable for performing an antigen-antibody reaction, such as phosphate buffered saline, a HEPES buffer, a PIPES buffer, a Tris buffer, etc.

Then, the user washes a surface of the working electrode body 62 of the electrode substrate 30 using the measurement solution [refer to the washing step in FIG. 5C]. In the step (C), the measurement solution is first added onto the working electrode body 62 of the electrode substrate 30 [refer to the step of addition of the measurement solution in FIG. 5C-1]. The substances which have not been captured by the capturing substance 81 [e.g., the labeling substance and the impurities (impurities F1, F2, F3)] are removed [refer to the step of removal of the impurities in FIG. 5C-2]. In the step (C), the washing step is performed using the measurement solution to be used in the step of addition of the measurement solution and the measurement step described later.

The measurement solution is a solution whose pH is set to a pH in which no electrostatic interaction occurs between the metal particle 92 and the working electrode 61 or a pH in which an electrostatic repulsive force occurs between the metal particle 92 and the working electrode 61, based on the zeta potentials of the metal particle 92 and the working electrode 61. The measurement solution is a solution containing an electrolyte.

Conventionally, when the test substance is detected based on the current resulting from the metal particle, an aqueous hydrochloric acid solution is used as the measurement solution after washing with the washing dedicated liquid, in order to efficiently perform the electrochemical oxidation of the metal particle, etc. As described above, the washing dedicated liquid has been conventionally used for the washing process. However, the present inventors have demonstrated that even when the washing step is performed using the conventional measurement solution in order to reduce variations in the measurement results from the residual of the washing dedicated liquid, highly accurate measurement is not possible (refer to Test Example 3 and FIG. 9 for details).

Then, the present inventors have developed, as a solution which can be used for washing and measurement, a solution whose pH is set so that no electrostatic interaction occurs between the metal particle and the working electrode or an electrostatic repulsive force occurs between the metal particle and the working electrode in the measurement solution based on the zeta potentials of the metal particle and the working electrode which are used for electrochemical measurement. In other words, the measurement solution to be used for the detection method according to one embodiment is set to the pH in which no electrostatic interaction occurs between the metal particle 92 and the working electrode 61 or the pH in which an electrostatic repulsive force occurs between the metal particle 92 and the working electrode 61, based on the zeta potentials of the metal particle 92 and the working electrode 61. Accordingly, it is considered that it is possible to prevent the (free) metal particle 92 which is not captured on the working electrode 61 from being nonspecifically adsorbed on the working electrode 61 through the capturing substance 81. Therefore, the detection method according to the present embodiment allows for an improvement in the accuracy of the detection of the test substance. The pH in which no electrostatic interaction occurs between the metal particle 92 and the working electrode 61 is specifically a pH in which the zeta potential of the metal particle 92 is 0 or a pH in which the surface potential of the working electrode 61 is 0. The pH in which no electrostatic interaction occurs between the metal particle 92 and the working electrode 61 or the pH in which an electrostatic repulsive force occurs between the metal particle 92 and the working electrode 61 is preferably a pH in which the zeta potential of the metal particle 92 and the zeta potential of the working electrode 61 have the same sign potential, from the viewpoint of preventing the metal particle from being nonspecifically adsorbed by electrostatic repulsion and reducing the noise.

The pH varies depending on the type of the conductive material forming the working electrode, the type of the metal particle, and the like. Accordingly, it is preferable to appropriately determine the pH in accordance with the type of the conductive material forming the working electrode, the type of the metal particle, and the like. Usually, the pH of the measurement solution is preferably 3.5 or more, more preferably 4 or more from the viewpoint of detecting the test substance at a high sensitivity. The pH is preferably 11 or less, more preferably 10 or less from the viewpoint of easy handling and excellent operability. Specifically, when the working electrode is, for example, a carbon-containing electrode, the pH of the measurement solution is preferably 3.5 or more, more preferably 4 or more from the viewpoint of detecting the test substance at a high sensitivity. The pH is preferably 11 or less, more preferably 10 or less from the viewpoint of easy handling and excellent operability. When the metal particle is, for example, a silver particle, the pH of the measurement solution is preferably 3.5 or more, more preferably 4 or more from the viewpoint of detecting the test substance at a high sensitivity. The pH is preferably 11 or less, more preferably 10 or less from the viewpoint of easy handling and excellent operability.

Examples of the electrolyte include sodium chloride, potassium chloride, sodium thiocyanate, and potassium thiocyanate. However, the present embodiment is not limited thereto.

Then, the user adds the measurement solution to the electrode substrate 30 after washing [refer to the step of addition of the measurement solution in FIG. 5D]. Thereafter, the user inserts the electrode substrate 30 into the substrate receiving unit 11 of the detector 1 shown in FIG. 1. Then, the user instructs the detector 1 to start the measurement, and the current from the metal particle is measured [refer to the measurement step in FIG. 5E]. The electrode leads 71, 73, and 75 of the electrode substrate 30 inserted into the detector 1 are connected to the ammeter 13 and the power source 14 of the detector 1. Then, an arbitrary potential based on the reference electrode 65 is applied to the working electrode body 62 by the power source 14 of the detector 1. Thereafter, a current value digitally converted by the A/D converting unit 15 is input into the control unit 16. Then, the control unit 16 estimates the amount of the test substance contained in the measurement sample from the digitally converted current value based on a calibration curve indicating a relationship between a current value created in advance and the amount of the test substance. The control unit 16 creates a detection result screen for displaying the information on the estimated amount of the test substance on the display 12. Thereafter, the detection result screen created by the control unit 16 is sent to the display 12 so as to be displayed on the display 12

In the step (D), the additive amount of the measurement solution may be a sufficient amount to measure the current.

In the step (E), the metal particle 92 is first electrochemically oxidized. The magnitude of the potential to be applied varies depending on the particle size of the metal particle 92, the type and concentration of the electrolyte added to the measurement solution, the pH of the measurement solution, or the like. Accordingly, it is desirable to appropriately determine the magnitude of the potential in accordance with the particle size of the metal particle 92, the type and concentration of the electrolyte added to the measurement solution, or the like. The time for applying the potential varies depending on the magnitude of the potential to be applied, the particle size of the metal particle 92, the type and concentration of the electrolyte added to the measurement solution, or the like. Accordingly, it is preferable to appropriately determine the time in accordance with the particle size of the metal particle 92, the type and concentration of the electrolyte added to the measurement solution, or the like. When the metal particle 92 is electrochemically oxidized, the potential may be kept at a constant value or may be changed with time.

The metal is deposited on a surface of the working electrode body 62 by eluting the metal particle 92 by electrochemical oxidation and electrochemically reducing metal ions. In the present embodiment, the test substance may be detected by measuring a current induced by reduction and using the obtained measurement result as an index. When the metal ions are electrochemically reduced, the metal ions in the measurement solution are electrochemically reduced on the surface of the working electrode body 62 by applying the potential to reduce the metal ions to the working electrode body 62, so that the metal can be deposited. When the metal ions are reduced, the metal may be deposited by applying the constant potential to electrochemically reduce the metal ions, maintaining the state, and electrochemically reducing the metal ions. Alternatively, the metal may be deposited by negatively changing the potential of the working electrode body 62 with time and electrochemically reducing the metal ions. Examples of the method of measuring a current induced by reducing metal ions include differential pulse voltammetry, cyclic voltammetry, and chronoamperometry. However, the present embodiment is not limited thereto.

In the detection method according to one embodiment, the test substance may be detected by electrochemically oxidizing the metal deposited on the surface of the working electrode body 62, measuring a current induced by the oxidation of the metal, and using the obtained measurement result as an index.

Examples of the method of electrochemically oxidizing the metal deposited on the surface of the working electrode body 62 and measuring the oxidation current include a method of positively changing the potential of the working electrode body 62 and measuring changes in the current due to the potential changes and a method of applying a constant potential to the working electrode body 62 and measuring the current change with respect to time. However, the present embodiment is not limited thereto. Examples of the method of measuring the current induced by oxidizing the metal include differential pulse voltammetry, cyclic voltammetry, and chronoamperometry. However, the present embodiment is not limited thereto.

Specifically, when the metal particle 92 is, for example, a silver particle, a silver particle 92a of the labeled complex 90 captured by the capturing substance on the working electrode body 62 of the working electrode 61 [refer to (a) of FIG. 6A] is oxidized to produce silver ions $92a1$ ($Ag^+$) in the measurement solution [refer to (b) of FIG. 6A]. The obtained silver ions 92a1 are reduced to deposit silver 92a2 on the surface of the working electrode substrate body. Thereafter, a current induced by converting the silver 92a2 to the silver ions 92a1 by oxidation is measured by the electrochemical measurement such as differential pulse voltammetry (DPV). When the metal particles 92 is, for example, a gold particle, a gold particle 92b of the labeled complex 90 captured by the capturing substance on the working electrode body 62 of the working electrode 61 [refer to (a) of FIG. 6B] is oxidized to produce gold ions $92b1$ ($Au^{3+}$) in the measurement solution [refer to (b) of FIG. 6B]. Thereafter, a current which has been induced when gold 92a2 is deposited on the surface of the working electrode substrate body by reduction of the eluted gold ions 92b1 is measured by the electrochemical measurement such as differential pulse voltammetry (DPV).

In the present embodiment, the voltage or electric charge may be measured as the electrical energy caused by oxidation reduction of metal, instead of measuring the current.

In the present embodiment, the detection method may be a method of detecting a test substance contained in a sample using a working electrode and a counter electrode, the method comprising:

(A) forming a complex that contains the test substance contained in the sample and a metal particle on the working electrode;

(B) washing the working electrode;

(C) adding a measurement solution to the working electrode and measuring a current, voltage or electric charge from the metal particle contained in the complex on the working electrode in the measurement solution by electrochemical measurement; and (D) detecting the test substance in the sample based on measurement results obtained in the step (C), wherein the step (B) includes washing the working electrode using a measurement solution having the same composition as the composition of the measurement solution used in the step (C) and the measurement solution has a pH of 3.5 or more. In the detection method, the measurement solution having a pH of 3.5 or more is used. Thus, it is possible to prevent the nonspecific metal particle causing the noise from being adsorbed on the working electrode and ensure sufficient detection sensitivity. In this case, the working electrode is preferably one containing a carbon material from the viewpoint of high chemical resistance and wide potential window.

EXAMPLES

Hereinafter, the present invention will be described in detail with reference to Examples and the like; however, the present invention is not limited thereto. Hereinafter, an antibody which recognizes an HBs antigen or CRP is referred to as an "HBs antigen-recognizing antibody or CRP-recognizing antibody, respectively".

Production Example 1

To 1 mg of graphite powder (product name: Graphite powder, manufactured by Sigma Aldrich Co. LLC.) was added 900 µL of carbonate buffer (pH 9.5). The graphite powder was dispersed by applying ultrasonic waves to the obtained mixture, followed by centrifugation at 6000 rpm and at room temperature for 5 minutes to remove the supernatant. To the obtained graphite powder was added 100 µL of carbonate buffer (pH 9.5) containing 100 µg/mL HBs antigen-recognizing antibody. The HBs antigen-recognizing antibody as the capturing substance 81 was immobilized on the graphite by allowing the obtained mixture to stand still at room temperature for 2 hours. The graphite having the HBs antigen-recognizing antibody immobilized thereon was washed with phosphate buffered saline. Then, 1000 µL of phosphate buffered saline containing 3 mass % fetal bovine serum albumin/5 mass % polyethylene glycol (Mw=20000) was added to the graphite to prepare a mixture. The surface of the graphite was blocked by allowing the obtained mixture to stand still at 4° C. overnight. Thus, antibody-immobilized graphite powder was obtained.

Production Example 2

A 1 M aqueous hydrochloric acid solution or a 1 M aqueous sodium hydroxide solution was added to 900 µL of aqueous silver nanoparticle dispersion (silver nanoparticle content: $1.7 \times 10^{10}$ particles/mL, average particle size: 60 nm, product name: Silver dispersion, Sigma Aldrich Co. LLC.) to adjust the pH of the aqueous silver nanoparticle dispersion to 7. Then, 100 µL of 10 mM phosphate buffer (pH 7.2) containing 100 µg/mL HBs antigen-recognizing antibody was added thereto. Thereafter, 10.1 µL of 10 vol % polyoxyethylene (20) sorbitan monolaurate solution [Tween 20 (registered trademark)] was added to the obtained solution. The HBs antigen-recognizing antibody was immobilized on the surface of the silver nanoparticle by allowing the obtained mixture to stand still at 4° C. for 1 hour. Thus, a suspension containing the labeled binding substance was obtained.

The labeled binding substance was blocked by adding 400 µL of TBS-T solution containing 1 mass % fetal bovine serum albumin to the obtained suspension and allowing the obtained mixture to stand still at 4° C. for 2 hours. After blocking, the mixture containing the labeled binding substance was subjected to centrifugation at 7000×g and at 4° C. for 20 minutes to remove the supernatant. To the obtained residue was added 1 mL of TBS-T solution containing 1 mass % fetal bovine serum albumin. The operation of subjecting the obtained mixture to centrifugation at 7000×g and at 4° C. for 20 minutes to remove the supernatant and adding TBS-T solution containing 1 mass % fetal bovine serum albumin to the obtained residue was repeated three times. Thereafter, the obtained mixture was subjected to centrifugation at 7000×g and at 4° C. for 20 minutes to remove the supernatant. To the obtained residue was added 200 µL of phosphate buffered saline containing 1 mass % fetal bovine serum albumin/0.01 vol % polyoxyethylene (20) sorbitan monolaurate to prepare a labeled binding substance-containing liquid.

Test Example 1

Figure 7A:
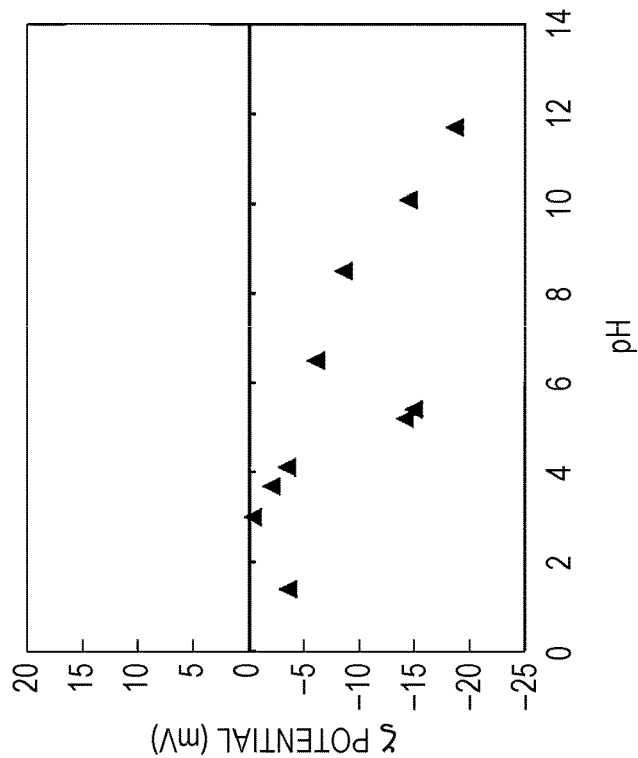
FIG. 7A is a graph showing the results obtained by examining the relationship between the zeta potential (ζ potential) of each of graphite and antibody-immobilized graphite and the pH of a measurement solution in Test Example 1.

The graphite powder and the antibody-immobilized graphite powder obtained in Production Example 1 serving as the components of the working electrode body and the counter electrode were added to 200 µL of measurement solution whose pH was adjusted to 1.4, 3, 3.7, 4.1, 5.2 or 10.1 (a solution containing 0.05 M chlorine). The zeta potentials of the graphite powder and the antibody-immobilized graphite powder in each of the obtained solutions were measured using Zetasizer (Zetasizer Nano ZS, Malvern Instruments Ltd.). FIG. 7A shows the results obtained by examining the relationship between the zeta potential ($\zeta$ potential) of each of the graphite powder and the antibody-immobilized graphite powder and the pH of the measurement solution in Test Example 1. In the Figure, each white circle represents the zeta potential of the graphite powder, meanwhile each black circle represents the zeta potential of the antibody-immobilized graphite powder.

Figure 7B:
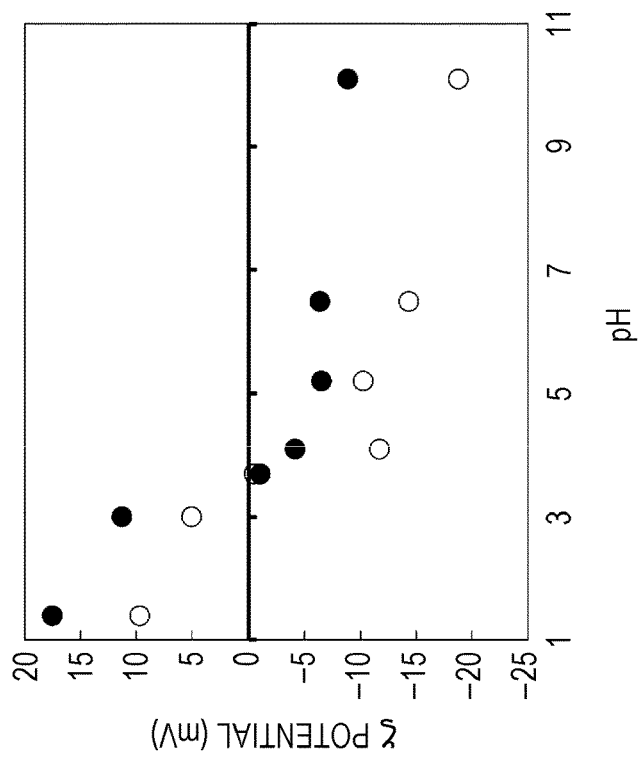
FIG. 7B is a graph showing the results obtained by examining the relationship between the zeta potential (ζ potential) of a labeled complex and the pH of the measurement solution in Test Example 1.

To 195 µL of the measurement solution whose pH was adjusted to 1.4, 3, 3.7, 4.1, 5.2, 5.4, 6.5, 8.5, 10.1 or 11.7 (a solution containing 0.05 M chlorine) was added 5 µL of the labeled binding substance-containing liquid obtained in Production Example 2. Then, the zeta potential of the silver particle serving as the metal particle of the labeled binding substance was measured using Zetasizer. FIG. 7B shows the results obtained by examining the relationship between the zeta potential ($\zeta$ potential) of the labeled binding substance and the pH of the measurement solution in Test Example 1. In the Figure, each black triangle represents the zeta potential of the silver particle.

The results shown in FIG. 7A indicate that the graphite powder and the antibody-immobilized graphite powder serving as the components of the working electrode body 62 and the counter electrode 63 are positively charged when the pH of the measurement solution is less than 3.5. It is found that when the pH of the measurement solution is around 3.5, the graphite powder and the antibody-immobilized graphite powder serving as the components of the working electrode body 62 and the counter electrode 63 are at the isoelectric point (potential: 0). It is confirmed that when the pH of the measurement solution is higher than 3.5, the graphite powder and the antibody-immobilized graphite powder serving as the components of the working electrode body 62 and the counter electrode 63 are negatively charged. On the other hand, the results shown in FIG. 7B indicate that the labeled binding substance is negatively charged. These results show the followings: when the measurement solution having a pH of less than 3.5 is used, the working electrode body 62 has a positive potential and the labeled binding substance (silver particle) has a negative potential. Thus, electrostatic attraction occurs between the working electrode body 62 and the labeled binding substance. When the measurement solution having a pH of around 3.5 is used, both the working electrode body 62 and the labeled binding substance have negative potentials. Thus, no electrostatic interaction occurs. Consequently, it is suggested that when the pH is higher than 3.5, an electrostatic repulsive force occurs between the working electrode body 62 and the labeled binding substance.

Production Example 3

(1) Formation of Electrodes

The working electrode 61 and the counter electrode 63 were formed by coating the surface of the substrate body 30a made of glass epoxy with a graphite powder-containing carbon paste to form a pattern shown in FIG. 4 and drying the surface. The reference electrode 65 made of silver/silver chloride was formed by coating the surface of the substrate body 30a with a silver/silver chloride ink. A resist insulating film (refer to 40 in FIG. 3) was disposed so that the working electrode body 62, the counter electrode 63, and the reference electrode 65 formed on the substrate body 30a were exposed.

(2) Immobilization of Capturing Substance

The HBs antigen-recognizing antibody as the capturing substance 81 was immobilized on the working electrode body 62 by dropping 3 μL of carbonate buffer (pH 9.5) containing 100 μg/mL HBs antigen-recognizing antibody on the working electrode body 62 of the electrode substrate 30 obtained in the step (1) and allowing the mixture to stand still under high humidity conditions of a relative humidity of 60% or more and at room temperature for 2 hours. The HBs antigen-recognizing antibody immobilized on the working electrode body 81 is an antibody which recognizes an antigen site different from that of the antibody which has been immobilized on the silver nanoparticle in Production Example 2.

(3) Blocking

In the above (2), the working electrode body 62 having the HBs antigen-recognizing antibody immobilized thereon was washed with phosphate buffered saline. Thereafter, the surface of the working electrode body 62 was blocked by dropping a blocking reagent [phosphate buffered saline containing 3 mass % fetal bovine serum albumin/5 mass % polyethylene glycol (Mw=20000)] on the working electrode body 62 and allowing the resultant to stand still under high humidity conditions of a relative humidity of 60% or more and at 4° C. overnight. Then, the blocking reagent was removed from the surface of the working electrode body 62. After that, the working electrode body 62 was washed with phosphate buffered saline, and thus the electrode substrate 30 was obtained.

Production Examples 4 and 5

An HBs antigen calibrator [manufactured by Sysmex Corporation] was added to fetal bovine serum so that the concentration of the HBs antigen was 0 IU/mL (Production Example 4) or 10 IU/mL (Production Example 5). Thus, simulated samples were prepared.

Test Example 2

The labeled binding substance-containing liquid obtained in Production Example 2 was mixed with the simulated sample obtained in each of Production examples 4 and 5 at a volume ratio of the labeled binding substance-containing liquid/the simulated sample of 1:1 to prepare a mixture. Subsequently, an antigen-antibody reaction was performed by dropping 4 μL of the mixture on the surface of the working electrode body 62 of the electrode substrate 30 obtained in Production Example 3 and allowing the resultant to stand still under high humidity conditions of a relative humidity of 60% or more and at room temperature for 1 hour.

After the antigen-antibody reaction, the working electrode 61 of the electrode substrate 30 was immersed in 200 μL of measurement solution whose pH was adjusted to 1.5, 3, 4.1, 5.3, 6.5 or 10.1 (a solution containing 0.05 M chlorine and sodium ions). Thereafter, the electrode substrate 30 was connected to a potentiostat. The measurement solution was dropped so as to cover the working electrode 61, the counter electrode 63, and the reference electrode 65. Then, the current was measured. In the current measurement, changes in current to changes in potential were measured by applying a potential of +2.1 V to the working electrode body 62 based on the reference electrode 65 for 30 seconds, applying a potential of −1 V to the body based on the reference electrode 65 for 140 seconds, and changing the potential of the working electrode body 62 from −0.4 V to +0.4 V by differential pulse voltammetry.

FIG. 8A shows the results obtained by examining the relationship between the current from the silver particles in the labeled complex which have been formed in a neighborhood of the surface of the working electrode and the pH of the measurement solution in Test Example 2, and FIG. 8B shows the results obtained by examining the relationship between the signal to noise ratio when measuring the current from the silver particles in the labeled complex which have been formed in a neighborhood of the surface of the working electrode and the pH of the measurement solution in Test Example 2. In FIG. 8A, white circle data points represent the current during the use of the simulated sample obtained in Production Example 4, meanwhile black circle data points represent the current during the use of the simulated sample obtained in Production Example 5. In FIG. 8B, black square data points represent the signal to noise ratio during the use of the simulated sample obtained in Production Example 5.

The results shown in FIG. 8 indicate that when the measurement solution having a pH of less than 3 is used, the nonspecific noise increases and the detection sensitivity (signal to noise ratio) decreases. On the other hand, it is found that when the measurement solution having a pH of greater than 3 is used, the nonspecific noise level is low. When the nonspecific noise level is low, the signal magnitude (current magnitude) can be increased by the potential to be applied. Accordingly, the results shown in FIG. 8 indicate that the detection sensitivity (signal to noise ratio) can be increased by washing the working electrode with the measurement solution having a pH greater than 3.

Production Example 6

An HBs antigen calibrator [manufactured by Sysmex Corporation] was adds to bovine serum so that the concentration of the HBs antigen was 25 IU/mL. Thus, a simulated sample was prepared.

Test Example 3

The labeled binding substance-containing liquid obtained in Production Example 2 was mixed with the simulated sample obtained in each of Production Examples 4 and 6 at a volume ratio of the labeled binding substance-containing liquid/the simulated sample of 1:1 to prepare a mixture. Subsequently, an antigen-antibody reaction was performed by dropping 4 μL of the mixture on the surface of the working electrode body 62 of the electrode substrate 30 obtained in Production Example 3 and allowing the resultant to stand still under high humidity conditions of a relative humidity of 60% or more and at room temperature for 1 hour. After the antigen-antibody reaction, the residual liquid of the mixture was removed from the working electrode body 62 of the electrode substrate 30. Then, the working electrode body 62 was washed with a washing dedicated liquid made of phosphate buffered saline. After washing, the working electrode body 62 was air-dried. Thereafter, the electrode substrate 30 was connected to a potentiostat. The measurement solution was dropped so as to cover the working electrode 61, the counter electrode 63, and the reference electrode 65. Then, the current was measured (Comparative Example 1).

The labeled binding substance-containing liquid obtained in Production Example 2 was mixed with the simulated sample obtained in each of Production Examples 4 and 6 at a volume ratio of the labeled binding substance-containing liquid/the simulated sample of 1:1 to prepare a mixture. Subsequently, an antigen-antibody reaction was performed by dropping 4 µL of the mixture on the surface of the working electrode body 62 of the electrode substrate 30 obtained in Production Example 3 and allowing the resultant to stand still under high humidity conditions of a relative humidity of 60% or more and at room temperature for 1 hour. After the antigen-antibody reaction, the working electrode 61 of the electrode substrate 30 was immersed in 200 µL of measurement solution (pH 1.2) containing 0.1 M hydrochloric acid. Thereafter, the electrode substrate 30 was connected to a potentiostat. The measurement solution was dropped so as to cover the working electrode 61, the counter electrode 63, and the reference electrode 65. Then, the current was measured (Comparative Example 2).

In the current measurement, changes in current to changes in potential were measured by applying a potential of +1.8 V to the working electrode body 62 based on the reference electrode 65 for 30 seconds, applying a potential of −0.8 V to the body based on the reference electrode 65 for 60 seconds, and changing the potential of the working electrode body 62 from −0.4 V to +0.4 V by differential pulse voltammetry.

Figure 9:
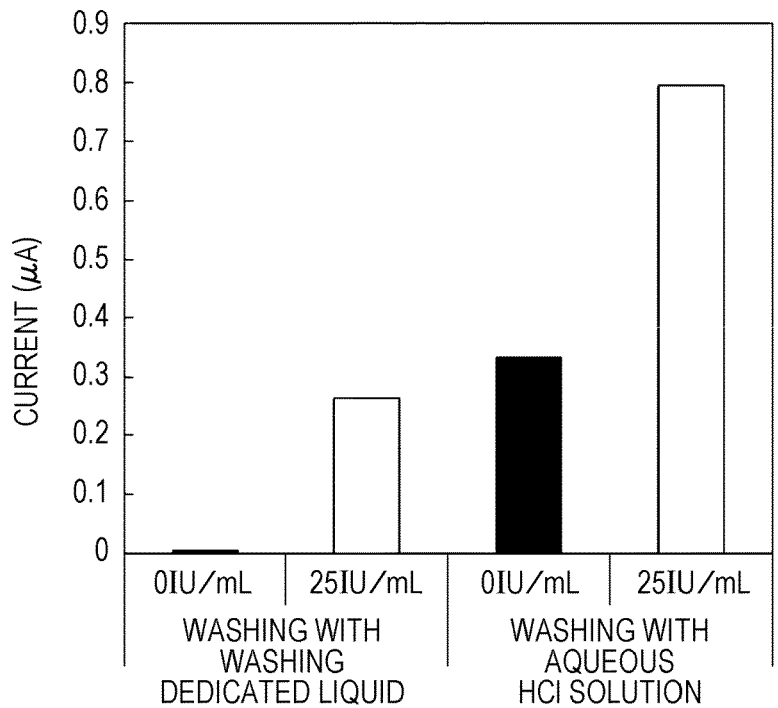
FIG. 9 is a graph showing the results obtained by examining the relationship between the current from silver particles in a labeled complex which have been formed in a neighborhood of a surface of a working electrode and the step of washing with a washing dedicated liquid or an aqueous hydrochloric acid solution in Test Example 3.

FIG. 9 shows the results obtained by examining the relationship between the current from the silver particles in the labeled complex which have been formed in a neighborhood of the surface of the working electrode and the step of washing with the washing dedicated liquid or the aqueous hydrochloric acid solution in Test Example 3.

The results shown in FIG. 9 indicate that, compared to the case where the steps of washing with the washing dedicated liquid made of phosphate buffered saline, removing the washing dedicated liquid, followed by drying are performed (Comparative Example 1), the noise increases when the washing step is performed using the conventional measurement solution containing hydrochloric acid. These results show that even if a solution which has been conventionally used as the measurement solution is used as the washing dedicated liquid for an attempt to commonalize the washing dedicated liquid and the measurement solution, it is not possible to measure the test substance at high accuracy.

Production Example 7

An HBs antigen calibrator [manufactured by Sysmex Corporation] was adds to bovine serum so that the concentration of the HBs antigen was 50 IU/mL. Thus, a simulated sample was prepared.

Test Example 4

The labeled binding substance-containing liquid obtained in Production Example 2 was mixed with the simulated sample obtained in each of Production Examples 4 and 7 at a volume ratio of the labeled binding substance-containing liquid/the simulated sample of 1:1 to prepare a mixture. Subsequently, an antigen-antibody reaction was performed by dropping 4 µL of the mixture on the surface of the working electrode body 62 of the electrode substrate 30 obtained in Production Example 3 and allowing the resultant to stand still under high humidity conditions of a relative humidity of 60% or more and at room temperature for 1 hour. After the antigen-antibody reaction, the working electrode 61 of the electrode substrate 30 was immersed in 200 µL of measurement solution (pH 5.3) containing 0.01 M potassium chloride. Thereafter, the electrode substrate 30 was connected to a potentiostat. The measurement solution was dropped so as to cover the working electrode 61, the counter electrode 63, and the reference electrode 65. Then, the current was measured (Example 1).

The labeled binding substance-containing liquid obtained in Production Example 2 was mixed with the simulated sample obtained in each of Production Examples 4 and 7 at a volume ratio of the labeled binding substance-containing liquid/the simulated sample of 1:1 to prepare a mixture. Subsequently, an antigen-antibody reaction was performed by dropping 4 µL of the mixture on the surface of the working electrode body 62 of the electrode substrate 30 obtained in Production Example 3 and allowing the resultant to stand still under high humidity conditions of a relative humidity of 60% or more and at room temperature for 1 hour. After the antigen-antibody reaction, the residual liquid of the mixture was removed from the working electrode body 62 of the electrode substrate 30. Then, the working electrode body 62 was washed with a washing dedicated liquid made of phosphate buffered saline. After washing, the working electrode body 62 was air-dried. Thereafter, the electrode substrate 30 was connected to a potentiostat. The measurement solution was dropped so as to cover the working electrode 61, the counter electrode 63, and the reference electrode 65. Then, the current was measured (Comparative Example 3).

In the current measurement, changes in current to changes in potential were measured by applying a potential of +1.8 V to the working electrode body 62 based on the reference electrode 65 for 30 seconds, applying a potential of −0.8 V to the body based on the reference electrode 65 for 60 seconds, and changing the potential of the working electrode body 62 from −0.4 V to +0.4 V by differential pulse voltammetry.

Figure 10:
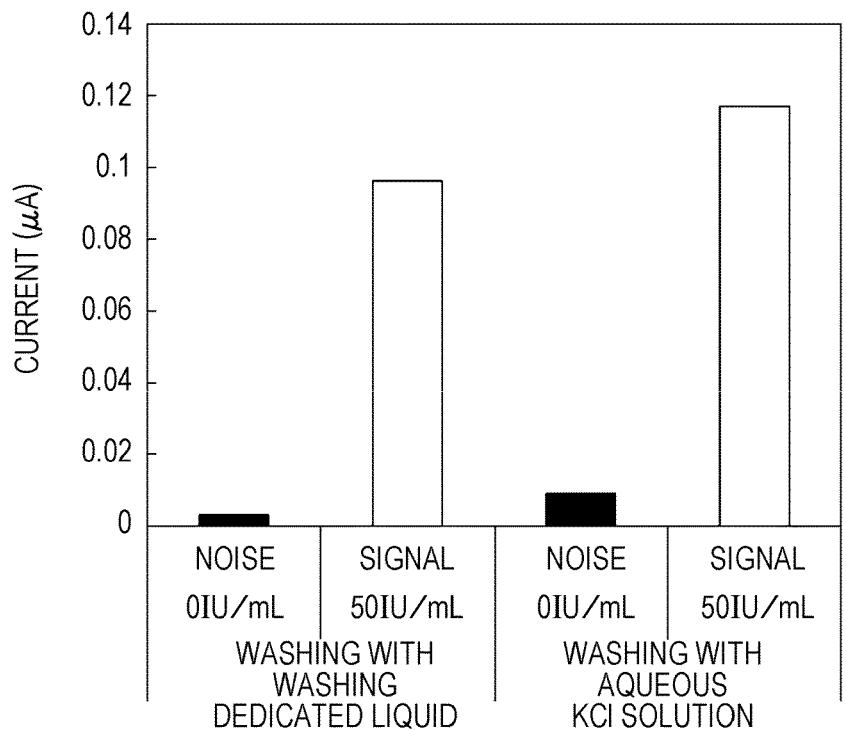
FIG. 10 is a graph showing the results obtained by examining the relationship between the current from silver particles in a labeled complex which have been formed in a neighborhood of a surface of a working electrode and the step of washing with a washing dedicated liquid or an aqueous potassium chloride solution in Test Example 4.

FIG. 10 shows the results obtained by examining the relationship between the current from the silver particles in the labeled complex which have been formed in a neighborhood of the surface of the working electrode and the step of washing with the washing dedicated liquid or the aqueous potassium chloride solution in Test Example 4.

The results shown in FIG. 10 indicate that when the washing step is performed using the measurement solution containing potassium chloride (Example 1), the obtained noise and signal levels are the same as those when the steps of washing with the washing dedicated liquid made of phosphate buffered saline, removing the washing dedicated liquid, followed by drying are performed (Comparative Example 3).

Production Example 8

An HBs antigen calibrator [manufactured by Sysmex Corporation] was adds to bovine serum so that the concentration of the HBs antigen was 12.5 IU/mL. Thus, a simulated sample was prepared.

Test Example 5

The labeled binding substance-containing liquid obtained in Production Example 2 was mixed with the simulated sample obtained in each of Production Examples 4 and 8 at a volume ratio of the labeled binding substance-containing liquid/the simulated sample of 1:1 to prepare a mixture. Subsequently, an antigen-antibody reaction was performed by dropping 4 µL of the mixture on the surface of the working electrode body 62 of the electrode substrate 30 obtained in Production Example 3 and allowing the resultant to stand still under high humidity conditions of a relative humidity of 60% or more and at room temperature for 1 hour. After the antigen-antibody reaction, the working electrode 61 of the electrode substrate 30 was immersed in 200 µL of measurement solution (pH 5.2) containing 0.05 M sodium chloride. Thereafter, the electrode substrate 30 was connected to a potentiostat. The measurement solution was dropped so as to cover the working electrode 61, the counter electrode 63, and the reference electrode 65. Then, the current was measured (Example 2).

The labeled binding substance-containing liquid obtained in Production Example 2 was mixed with the simulated sample obtained in each of Production Examples 4 and 8 at a volume ratio of the labeled binding substance-containing liquid/the simulated sample of 1:1 to prepare a mixture. Subsequently, an antigen-antibody reaction was performed by dropping 4 µL of the mixture on the surface of the working electrode body 62 of the electrode substrate 30 obtained in Production Example 3 and allowing the resultant to stand still under high humidity conditions of a relative humidity of 60% or more and at room temperature for 1 hour. After the antigen-antibody reaction, the residual liquid of the mixture was removed from the working electrode body 62 of the electrode substrate 30. Then, the working electrode body 62 was washed with a washing dedicated liquid made of phosphate buffered saline. After washing, the working electrode body 62 was air-dried. Thereafter, the electrode substrate 30 was connected to a potentiostat. The measurement solution was dropped so as to cover the working electrode 61, the counter electrode 63, and the reference electrode 65. Then, the current was measured (Comparative Example 4).

In the current measurement, changes in current to changes in potential were measured by applying a potential of +2.1 V to the working electrode body 62 based on the reference electrode 65 for 30 seconds, applying a potential of −1.0 V to the body based on the reference electrode 65 for 140 seconds, and changing the potential of the working electrode body 62 from −0.4 V to +0.4 V by differential pulse voltammetry.

Figure 11:
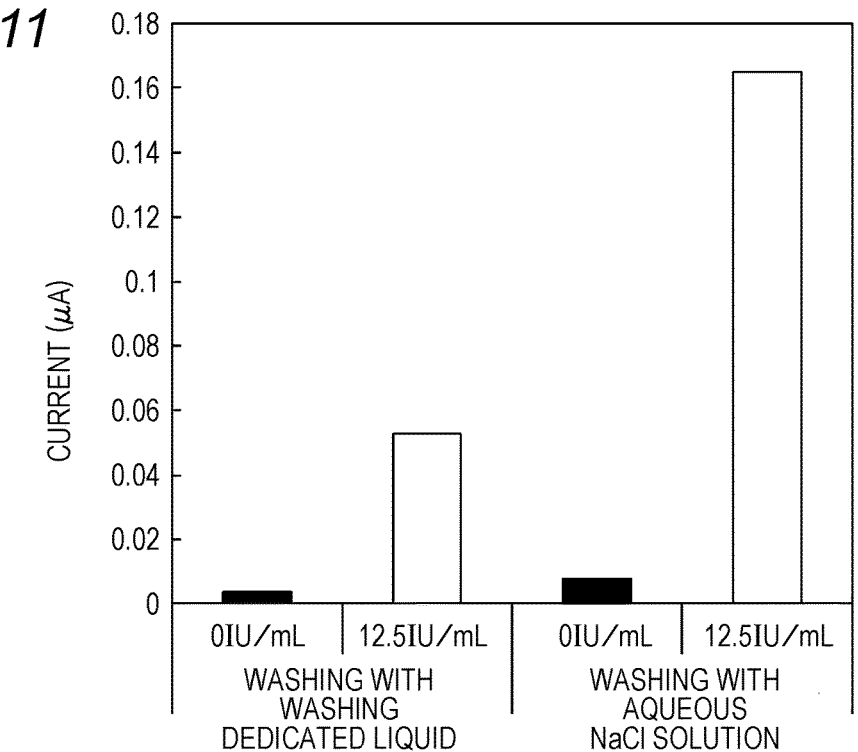
FIG. 11 is a graph showing the results obtained by examining the relationship between the current from silver particles in a labeled complex which have been formed in a neighborhood of a surface of a working electrode and the step of washing with a washing dedicated liquid or an aqueous sodium chloride solution in Test Example 5.

FIG. 11 shows the results obtained by examining the relationship between the current from the silver particles in the labeled complex which have been formed in a neighborhood of the surface of the working electrode and the step of washing with the washing dedicated liquid or the aqueous sodium chloride solution in Test example 5;

The results shown in FIG. 11 indicate that when the washing step is performed using the measurement solution containing sodium chloride (Example 2), the noise level is the same as that and the signal level is higher than that when the steps of washing with the washing dedicated liquid made of phosphate buffered saline, removing the washing dedicated liquid, followed by drying are performed (Comparative Example 4).

Test Example 6

The labeled binding substance-containing liquid obtained in Production Example 2 was mixed with the simulated sample obtained in Production Example 8 at a volume ratio of the labeled binding substance-containing liquid/the simulated sample of 1:1 to prepare a mixture. Subsequently, an antigen-antibody reaction was performed by dropping 4 µL of the mixture on the surface of the working electrode body 62 of the electrode substrate 30 obtained in Production Example 3 and allowing the resultant to stand still under high humidity conditions of a relative humidity of 60% or more and at room temperature for 1 hour. After the antigen-antibody reaction, the residual liquid of the mixture was removed from the working electrode body 62 of the electrode substrate 30. Then, the working electrode body 62 was washed with a washing dedicated liquid made of phosphate buffered saline. After washing, the working electrode body 62 was air-dried. Thereafter, the electrode substrate 30 was connected to a potentiostat. The measurement solution was dropped so as to cover the working electrode 61, the counter electrode 63, and the reference electrode 65. Then, the current was measured. The same experiment was further performed three times (Comparative Example 5).

The labeled binding substance-containing liquid obtained in Production Example 2 was mixed with the simulated sample obtained in Production Example 8 at a volume ratio of the labeled binding substance-containing liquid/the simulated sample of 1:1 to prepare a mixture. Subsequently, an antigen-antibody reaction was performed by dropping 4 µL of the mixture on the surface of the working electrode body 62 of the electrode substrate 30 obtained in Production Example 3 and allowing the resultant to stand still under high humidity conditions of a relative humidity of 60% or more and at room temperature for 1 hour. After the antigen-antibody reaction, the working electrode 61 of the electrode substrate 30 was immersed in 200 µL of measurement solution (pH 5.2) containing 0.05 M sodium chloride. Thereafter, the electrode substrate 30 was connected to a potentiostat. The measurement solution was dropped so as to cover the working electrode 61, the counter electrode 63, and the reference electrode 65. Then, the current was measured. The same experiment was further performed twice (Example 3).

Figure 12:
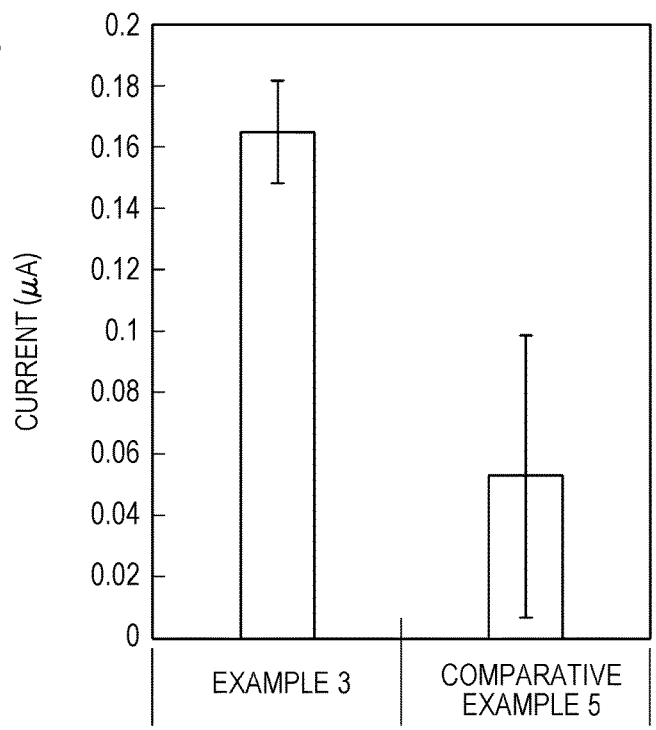
FIG. 12 is a graph showing the results of Example 3 and Comparative Example 5.

FIG. 12 shows the results of Example 3 and Comparative Example 5;

As shown in FIG. 12, the CV value of the measurement result of Example 3 was 10% and the CV value of the measurement result of Comparative example 5 was 85%. These results show that the CV value of the measurement result increases when the steps of washing with the washing dedicated liquid made of phosphate buffered saline, removing the washing dedicated liquid, followed by drying are performed (Comparative Example 5), and thus the variations in the signal occur for each measurement. On the other hand, when the washing step was performed using the measurement solution containing sodium chloride (Example 3), the CV value was low and no variation in the signal occurred. Thus, this shows excellent reproducibility.

Production Examples 9 and 10

An HBs antigen calibrator [manufactured by Sysmex Corporation] was added to bovine serum so that the concentration of the HBs antigen was 1.56 IU/mL (Production Example 9) or 6.25 IU/mL (Production Example 10). Thus, simulated samples were prepared.

Test Example 7

The labeled binding substance-containing liquid obtained in Production Example 2 was mixed with the simulated sample obtained in each of Production Example 4 (HBs-antigen concentration: 0 IU/mL), Production Example 9 (HBs-antigen concentration: 1.56 IU/mL), Production Example 9 (HBs-antigen concentration: 6.25 IU/mL) and Production Example 6 (HBs-antigen concentration: 25 IU/mL) at a volume ratio of the labeled binding substance-containing liquid/the simulated sample of 1:1 to prepare a mixture. Subsequently, an antigen-antibody reaction was performed by dropping 4 μL of the mixture on the surface of the working electrode body 62 of the electrode substrate 30 obtained in Production Example 3 and allowing the resultant to stand still under high humidity conditions of a relative humidity of 60% or more and at room temperature for 1 hour. After the antigen-antibody reaction, the working electrode 61 of the electrode substrate 30 was immersed in 200 μL of measurement solution (pH 5.2) containing 0.05 M sodium chloride. Thereafter, the electrode substrate 30 was connected to a potentiostat. The measurement solution was dropped so as to cover the working electrode 61, the counter electrode 63, and the reference electrode 65. Then, the current was measured (Example 4).

The labeled binding substance-containing liquid obtained in Production Example 2 was mixed with the simulated sample obtained in each of Production Example 4 (HBs-antigen concentration: 0 IU/mL), Production Example 9 (HBs-antigen concentration: 1.56 IU/mL), Production Example 10 (HBs-antigen concentration: 6.25 IU/mL) and Production Example 6 (HBs-antigen concentration: 25 IU/mL) at a volume ratio of the labeled binding substance-containing liquid/the simulated sample of 1:1 to prepare a mixture. Subsequently, an antigen-antibody reaction was performed by dropping 4 μL of the mixture on the surface of the working electrode body 62 of the electrode substrate 30 obtained in Production Example 3 and allowing the resultant to stand still under high humidity conditions of a relative humidity of 60% or more and at room temperature for 1 hour. After the antigen-antibody reaction, the working electrode 61 of the electrode substrate 30 was immersed in 200 μL of measurement solution (pH 1.2) containing 0.05 M hydrochloric acid. Thereafter, the electrode substrate 30 was connected to a potentiostat The measurement solution was dropped so as to cover the working electrode 61, the counter electrode 63, and the reference electrode 65. Then, the current was measured (Comparative Example 6).

In the current measurement, changes in current to changes in potential were measured by applying a potential of +2.1 V to the working electrode body 62 based on the reference electrode 65 for 30 seconds, applying a potential of −1.0 V to the body based on the reference electrode 65 for 140 seconds, and changing the potential of the working electrode body 62 from −0.4 V to +0.4 V by differential pulse voltammetry.

Figure 13:
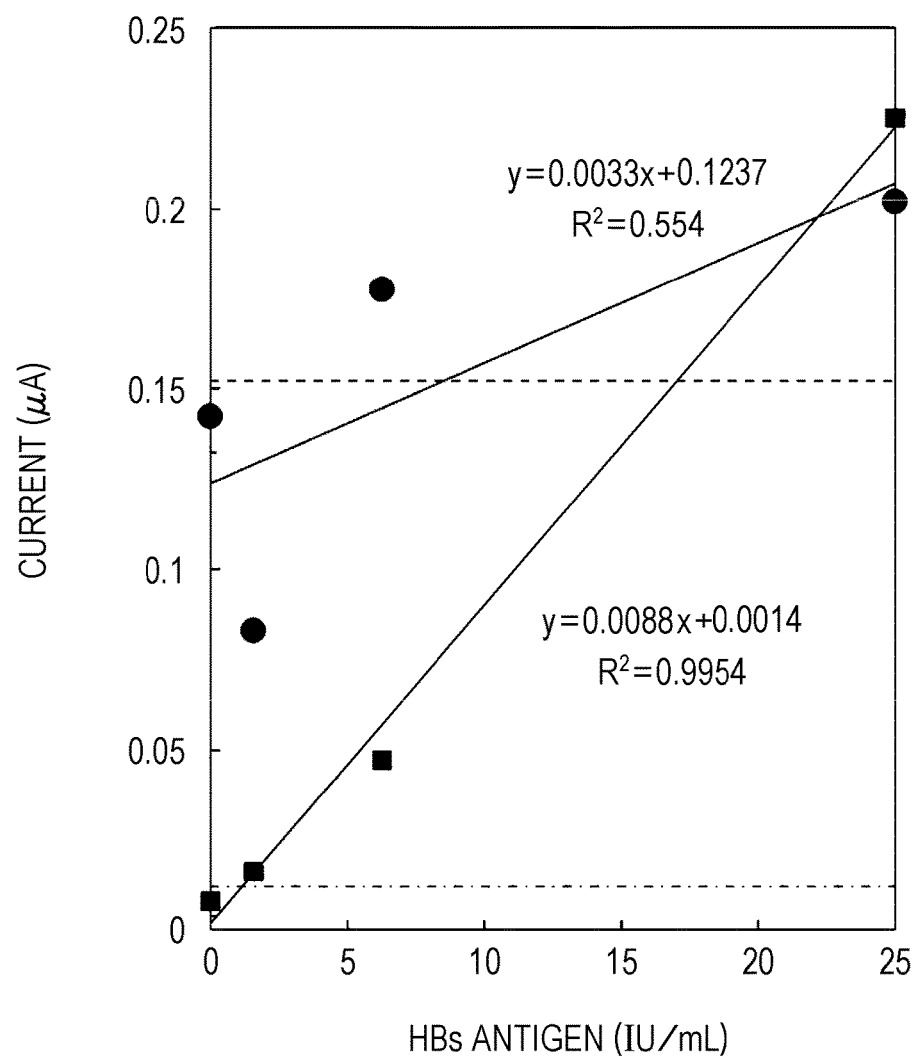
FIG. 13 is a graph showing the results obtained by examining the relationship between the current from silver particles in a labeled complex which have been formed in a neighborhood of a surface of a working electrode after washing with an aqueous hydrochloric acid solution or an aqueous sodium chloride solution and the amount of HBs antigen in Test Example 7.

FIG. 13 shows the results obtained by examining the relationship between the current from the silver particles in the labeled complex which have been formed in a neighborhood of the surface of the working electrode after washing with the aqueous hydrochloric acid solution or the aqueous sodium chloride solution and the amount of HBs antigen in Test Example 7. In the Figure, black circle data point represents the current from the silver particles in the labeled complex which have been formed in a neighborhood of the surface of the working electrode after washing with the aqueous hydrochloric acid solution, and black square data point represents the current from the silver particles in the labeled complex which have been formed in a neighborhood of the surface of the working electrode after washing with the aqueous sodium chloride solution.

The results shown in FIG. 13 indicate that when the measurement solution containing 0.05 M hydrochloric acid is used as the measurement solution (Comparative Example 6), the noise level was high, there was a weak proportional relationship between the amount of the HBs antigen and the magnitude of the current, and a low concentration of the HBs antigen is not detectable. On the other hand, it was found that when the measurement solution containing 0.05 M sodium chloride was used as the measurement solution (Example 4), the noise level was low, there was a strong proportional relationship between the amount of the HBs antigen and the magnitude of the current, and a low concentration of the HBs antigen was detectable.

Production Example 11

A 5 M aqueous sodium hydroxide solution was added to 900 μL of aqueous silver nanoparticle dispersion (silver nanoparticle content: $4.5 \times 10^{11}$ particles/mL, average particle size: 20 nm, product name: Silver dispersion, Sigma Aldrich Co. LLC.) to adjust the pH of the silver nanoparticle dispersion to 9. Then, 100 μL of 10 mM phosphate buffer (pH 7.2) containing 100 μg/mL CRP-recognizing antibody was added thereto. Thereafter, 10.1 μL of 10 vol % polyoxyethylene (20) sorbitan monolaurate solution [Tween 20 (registered trademark)] was added to the obtained solution. The CRP-recognizing antibody was immobilized on the surface of the silver nanoparticle by allowing the obtained mixture to stand still at 4° C. for 1 hour. Thus, a suspension containing the labeled binding substance was obtained.

The labeled binding substance was blocked by adding 400 μL of TBS-T solution containing 1 mass % fetal bovine serum albumin to the obtained suspension and allowing the obtained mixture to stand still at 4° C. for 2 hours. After blocking, the mixture containing the labeled binding substance was subjected to centrifugation at 15000×g and at 4° C. for 30 minutes to remove the supernatant. To the obtained residue was added 1 mL of TBS-T solution containing 1 mass % fetal bovine serum albumin. The operation of subjecting the obtained mixture to centrifugation at 15000×g and at 4° C. for 30 minutes to remove the supernatant and adding TBS-T solution containing 1 mass % fetal bovine serum albumin to the obtained residue was repeated twice. Thereafter, the obtained mixture was subjected to centrifugation at 15000×g and at 4° C. for 30 minutes to remove the supernatant. To the obtained residue was added 200 μL of phosphate buffered saline containing 5 mass % fetal bovine serum albumin/0.01 vol % polyoxyethylene (20) sorbitan monolaurate to prepare a labeled binding substance-containing liquid.

Production Example 12

(1) Formation of Electrodes

The working electrode 61 and the counter electrode 63 were formed by coating the surface of the substrate body 30a made of glass epoxy with a graphite powder-containing carbon paste to form a pattern shown in FIG. 4 and drying the surface. The reference electrode 65 made of silver/silver chloride was formed by coating the surface of the substrate body 30a with a silver/silver chloride ink. A resist insulating film (refer to 40 in FIG. 3) was disposed so that the working electrode body 62, the counter electrode 63, and the reference electrode 65 formed on the substrate body 30a were exposed.

(2) Immobilization of Capturing Substance

The CRP-recognizing antibody as the capturing substance 81 was immobilized on the working electrode body 62 by dropping 3 μL of carbonate buffer (pH 9.5) containing 100 μg/mL of CRP-recognizing antibody on the working electrode body 62 of the electrode substrate 30 obtained in the step (1) and allowing the mixture to stand still under high humidity conditions of a relative humidity of 60% or more and at room temperature for 2 hours. The CRP-recognizing antibody immobilized on the working electrode body 81 is an antibody which recognizes an antigen site different from that of the antibody which has been immobilized on the silver nanoparticle in Production Example 11.

(3) Blocking

In the above (2), the working electrode body 62 having the CRP-recognizing antibody immobilized thereon was washed with phosphate buffered saline. Thereafter, the surface of the working electrode body 62 was blocked by dropping a blocking reagent [phosphate buffered saline containing 5 mass % fetal bovine serum albumin/1 mass % polyethylene glycol (Mw=20000)] on the working electrode body 62 and allowing the resultant to stand still under high humidity conditions of a relative humidity of 60% or more and at 4° C. overnight. Then, the blocking reagent was removed from the surface of the working electrode body 62. After that, the working electrode body 62 was washed with phosphate buffered saline, and thus the electrode substrate 30 was obtained.

Production Examples 13 to 21

Simulated samples were produced by adding respective CRP calibrators (manufactured by SEKISUI MEDICAL CO., LTD.) to physiological saline so that the CRP concentration was 0 mg/dL (Production Example 13), 0.001 mg/dL (Production Example 14), 0.004 mg/dL (Production Example 15), 0.01 mg/dL (Production Example 16), 0.04 mg/dL (Production Example 17), 0.1 mg/dL (Production Example 18), 0.4 mg/dL (Production Example 19), 1.2 mg/dL (Production Example 20) or 3.6 mg/dL (Production Example 21).

Test Example 8

The labeled binding substance-containing liquid obtained in Production Example 2 was mixed with a solution (simulated sample) obtained by 10-fold diluting each of the simulated samples obtained in Production Example 13 (CRP concentration: 0 mg/dL), Production Example 14 (CRP concentration: 0.001 mg/dL), Production Example 15 (CRP concentration: 0.004 mg/dL), Production Example 16 (CRP concentration: 0.01 mg/dL), Production Example 17 (CRP concentration: 0.04 mg/dL), Production Example 18 (CRP concentration: 0.1 mg/dL), Production Example 19 (CRP concentration: 0.4 mg/dL), Production Example 20 (CRP concentration: 1.2 mg/dL) and Production Example 21 (CRP concentration: 3.6 mg/dL) with a diluent [R1 reagent of "ss Pure," manufactured by SEKISUI MEDICAL CO., LTD.] at a volume ratio of the labeled binding substance-containing liquid/the simulated sample of 1:1 to prepare a mixture. Subsequently, an antigen-antibody reaction was performed by dropping 4 μL of the mixture on the surface of the working electrode body 62 of the electrode substrate 30 obtained in Production Example 3 and allowing the resultant to stand still under high humidity conditions of a relative humidity of 60% or more and at room temperature for 25 minutes. After the antigen-antibody reaction, the working electrode 61 of the electrode substrate 30 was immersed in 200 μL of measurement solution (pH 5.2) containing 0.05 M sodium chloride. Thereafter, the electrode substrate 30 was connected to a potentiostat. The measurement solution was dropped so as to cover the working electrode 61, the counter electrode 63, and the reference electrode 65. Then, the current was measured (Example 5).

In the current measurement, changes in current to changes in potential were measured by applying a potential of +2.1 V to the working electrode body 62 based on the reference electrode 65 for 30 seconds, applying a potential of −1.0 V to the body based on the reference electrode 65 for 140 seconds, and changing the potential of the working electrode body 62 from −0.4 V to +0.4 V by differential pulse voltammetry.

Figure 14:
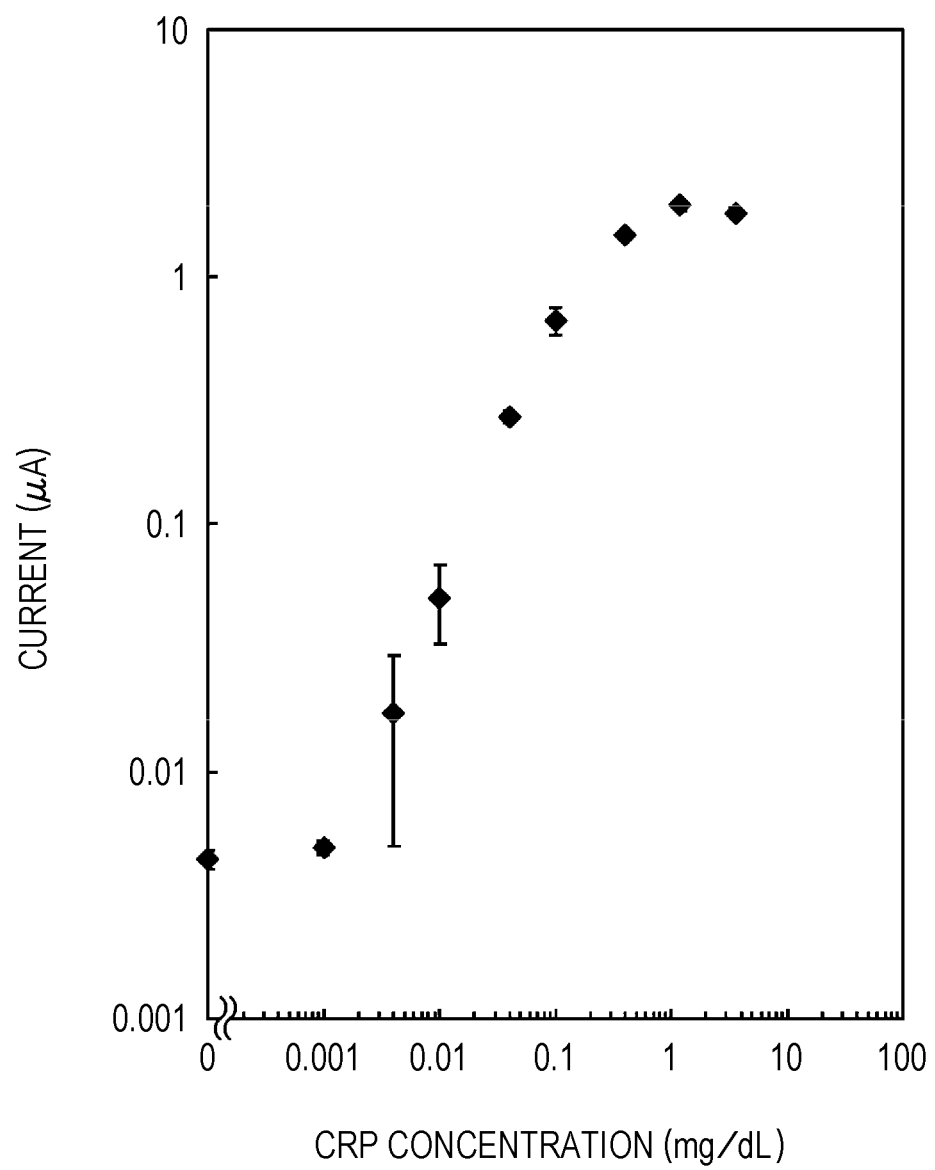
FIG. 14 is a graph showing the results obtained by examining the relationship between the current from silver particles in a labeled complex which have been formed in a neighborhood of a surface of a working electrode after washing with a measurement solution and the concentration of CRP (C-reactive protein) in Test Example 8.

FIG. 14 shows the results obtained by examining the relationship between the current from the silver particles in the labeled complex which have been formed in a neighborhood of the surface of the working electrode after washing with the measurement solution and the concentration of CRP in Test Example 8.

The results shown in FIG. 14 indicate that even if the test substance is CRP, the test substance can be quantitatively detected at high sensitivity by washing with the measurement solution in this example.

Production Example 22

A 5 M aqueous sodium hydroxide solution was added to 900 μL of aqueous silver nanoparticle dispersion (silver nanoparticle content: $4.5 \times 10^{11}$ particles/mL, average particle size: 20 nm, product name: Silver dispersion, Sigma Aldrich Co. LLC.) to adjust the pH of the aqueous silver nanoparticle dispersion to 9. Then, 100 μL of 10 mM phosphate buffer (pH 7.2) containing 100 μg/mL of CRP-recognizing antibody was added thereto. Thereafter, 10.1 μL of 10 vol % polyoxyethylene (20) sorbitan monolaurate solution [Tween 20 (registered trademark)] was added to the obtained solution. The CRP-recognizing antibody was immobilized on the surface of the silver nanoparticle by allowing the obtained mixture to stand still at 4° C. for 1 hour. Thus, a suspension containing the labeled binding substance was obtained.

The labeled binding substance was blocked by adding 400 μL of TBS-T solution containing 1 mass % fetal bovine serum albumin to the obtained suspension and allowing the obtained mixture to stand still at 4° C. for 2 hours. After blocking, the mixture containing the labeled binding substance was subjected to centrifugation at 15000×g and at 4° C. for 30 minutes to remove the supernatant. To the obtained residue was added 1 mL of TBS-T solution containing 1 mass % fetal bovine serum albumin. The operation of subjecting the obtained mixture to centrifugation at 15000×g and at 4° C. for 30 minutes to remove the supernatant and adding TBS-T solution containing 1 mass % fetal bovine serum albumin to the obtained residue was repeated twice. Thereafter, the obtained mixture was subjected to centrifugation at 15000×g and at 4° C. for 30 minutes to remove the supernatant. To the obtained residue was added 200 μL of phosphate buffered saline containing 5 mass % fetal bovine serum albumin/0.01 vol % polyoxyethylene (20) sorbitan monolaurate. The obtained solution (180 μL) was subjected to centrifugation at 15000×g and at 4° C. for 30 minutes to remove 150 μL of the supernatant. Then, a labeled binding substance-containing liquid was prepared.

Test Example 9

The labeled binding substance-containing liquid obtained in Production Example 2 was mixed with a solution (simulated sample) obtained by 10-fold diluting each of the simulated samples obtained in Production Example 13 (CRP concentration: 0 mg/dL), Production Example 15 (CRP concentration: 0.004 mg/dL), Production Example 17 (CRP concentration: 0.04 mg/dL), Production Example 19 (CRP concentration: 0.4 mg/dL), Production Example 20 (CRP concentration: 1.2 mg/dL) and Production Example 21 (CRP concentration: 3.6 mg/dL) with a diluent [product name: R1 reagent of "ss Pure", manufactured by SEKISUI MEDICAL CO., LTD.] at a volume ratio of the labeled binding substance-containing liquid/the simulated sample of 1:1 to prepare a mixture. Subsequently, an antigen-antibody reaction was performed by dropping 4 μL of the mixture on the surface of the working electrode body 62 of the electrode substrate 30 obtained in Production Example 3 and allowing the resultant to stand still under high humidity conditions of a relative humidity of 60% or more and at room temperature for 25 minutes. After the antigen-antibody reaction, the working electrode 61 of the electrode substrate 30 was immersed in 200 μL of measurement solution (pH 5.2) containing 0.05 M sodium chloride. Thereafter, the electrode substrate 30 was connected to a potentiostat. The measurement solution was dropped so as to cover the working electrode 61, the counter electrode 63, and the reference electrode 65. Then, the current was measured (Example 6).

In the current measurement, changes in current to changes in potential were measured by applying a potential of +2.1 V to the working electrode body 62 based on the reference electrode 65 for 30 seconds, applying a potential of −1.0 V to the body based on the reference electrode 65 for 140 seconds, and changing the potential of the working electrode body 62 from −0.4 V to +0.4 V by differential pulse voltammetry.

Figure 15:
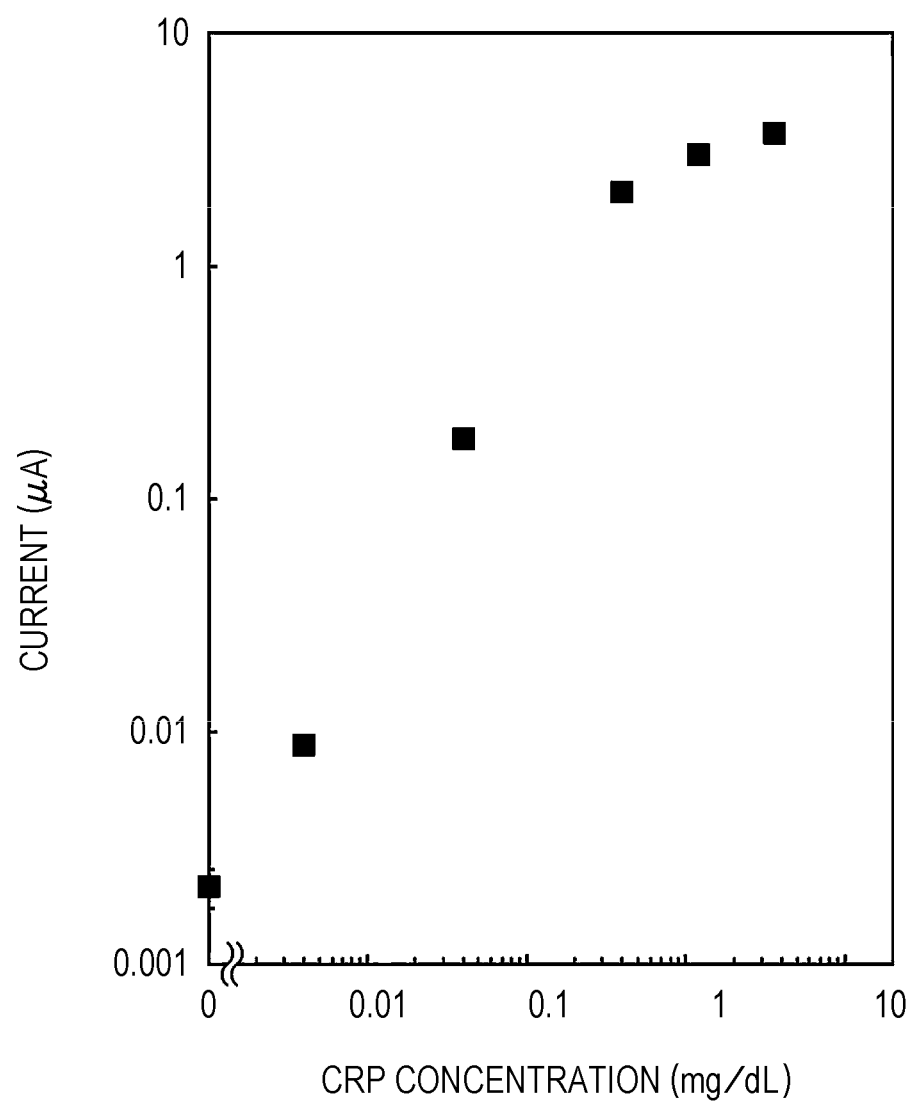
FIG. 15 is a graph showing the results obtained by examining the relationship between the current from silver particles in a labeled complex which have been formed in a neighborhood of a surface of a working electrode after using a labeled binding substance having a high concentration and washing with a measurement solution and the concentration of CRP in Test Example 9.

FIG. 15 shows the results obtained by examining the relationship between the current from the silver particles in the labeled complex which have been formed in a neighborhood of the surface of the working electrode after using a labeled binding substance having a high concentration and washing with the measurement solution and the concentration of CRP in Test Example 9.

The results shown in FIG. 15 indicate that even if the labeled binding substance having a high concentration is used, the CRP as the test substance can be quantitatively detected at high sensitivity in a wide measurement range without causing an increase in noise by washing with the measurement solution in this example.

Test Example 10

The labeled binding substance-containing liquid obtained in Production Example 2 was mixed with the simulated sample obtained in each of Production Example 4 and 6 at a volume ratio of the labeled binding substance-containing liquid/the simulated sample of 1:1 to prepare a mixture. Subsequently, an antigen-antibody reaction was performed by dropping 4 μL of the mixture on the surface of the working electrode body 62 of the electrode substrate 30 obtained in Production Example 3 and allowing the resultant to stand still under high humidity conditions of a relative humidity of 60% or more and at room temperature for 1 hour.

After the antigen-antibody reaction, the working electrode 61 of the electrode substrate 30 was immersed in 200 μL of measurement solution whose pH was adjusted to 3, 3.7 or 4.1 (a solution containing 0.05 M chloride). Thereafter, the electrode substrate 30 was connected to a potentiostat. The measurement solution was dropped so as to cover the working electrode 61, the counter electrode 63, and the reference electrode 65. Then, the current was measured. In the current measurement, changes in current to changes in potential were measured by applying a potential of +2.1 V to the working electrode body 62 based on the reference electrode 65 for 30 seconds, applying a potential of −1.0 V to the body based on the reference electrode 65 for 140 seconds, and changing the potential of the working electrode body 62 from −0.4 V to +0.4 V by differential pulse voltammetry.

Figure 16:
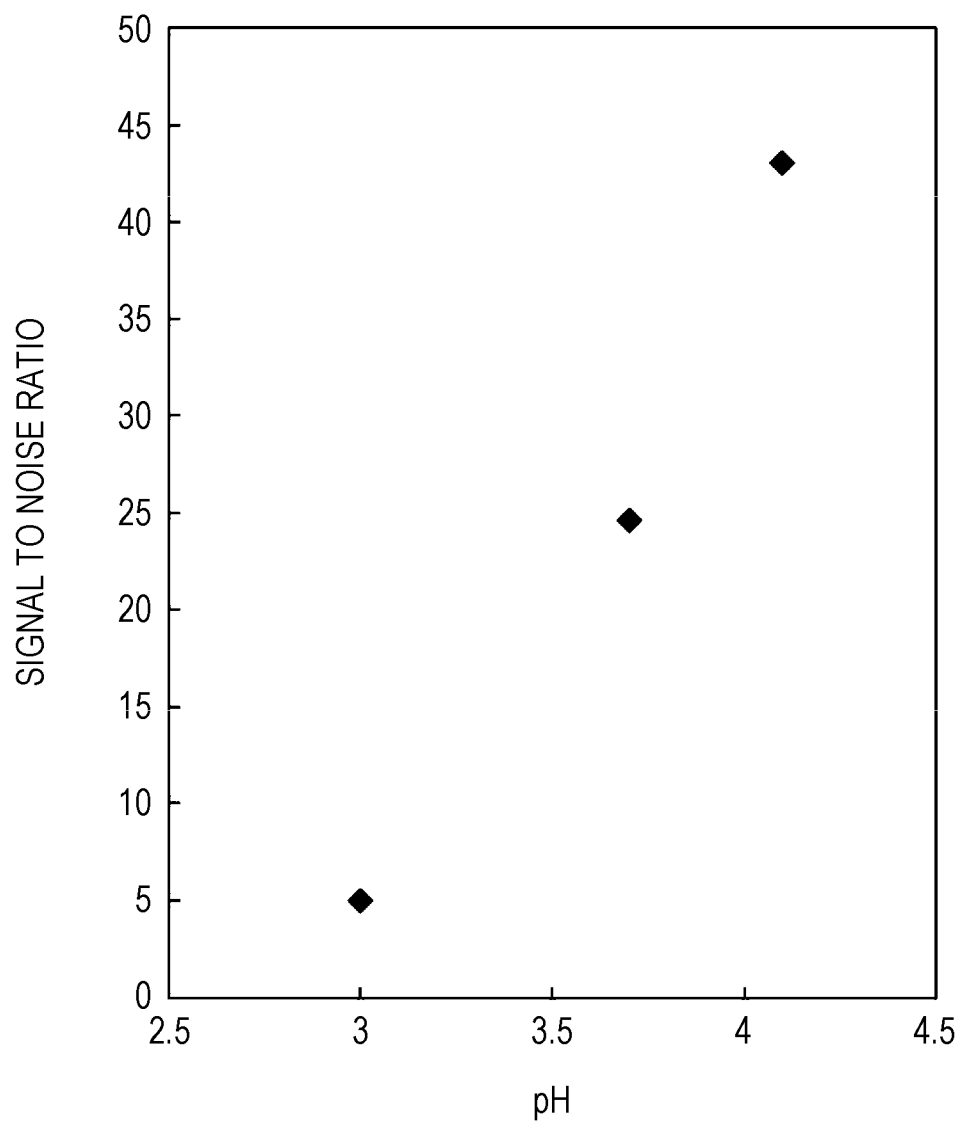
FIG. 16 is a graph showing the results obtained by examining the relationship between the signal to noise ratio when measuring the current from silver particles in a labeled complex which have been formed in a neighborhood of a surface of a working electrode and the pH of a measurement solution in Test Example 10.

Table 1 shows the results obtained by measuring the noise and signal from the silver particles in the labeled complex which have been formed in a neighborhood of the surface of the working electrode after washing with each measurement solution. FIG. 16 shows the results obtained by examining the relationship between the signal to noise ratio when measuring the current from the silver particles in the labeled complex which have been formed in a neighborhood of the surface of the working electrode and the pH of the measurement solution in Test Example 10.

TABLE 1

| pH | Noise (μA) (HBs concentration: 0 IU/mL) | Signal (μA) (HBs concentration: 50 IU/mL) |
|---|---|---|
| 3 | 0.08361 | 0.5005 |
| 3.7 | 0.02888 | 0.7404 |
| 4.1 | 0.007284 | 0.3209 |

The results shown in Table 1 and FIG. 16 indicate that when the measurement solution having a pH of 3 is used, the noise increases and the detection sensitivity (signal to noise ratio) decreases. On the other hand, when the measurement solution having a pH of 3.5 or more is used, the noise level is low. This shows that the detection sensitivity is high. As described above, when the nonspecific noise level is low, the signal size (magnitude of current) can be increased by the electrochemical conditions to be applied. Accordingly, the results shown in FIG. 8 indicate that the detection sensitivity (signal to noise ratio) can be increased by washing the working electrode with the measurement solution having a pH of 3.5 or more.

The above results suggest that, according to the method of detecting a test substance of the present invention, the method comprising the step of washing a working electrode with a measurement solution which has the same composition as that of the measurement solution used for the current measurement and whose pH is set to a pH in which no electrostatic interaction occurs between the metal particle and the working electrode or a pH in which an electrostatic repulsive force occurs between the metal particle and the working electrode, based on the zeta potentials of the metal particle and the working electrode, it is possible to suppress the variations in the accuracy of the detection of the test substance and to ensure the same detection sensitivity as that when a washing dedicated liquid is used, without using the washing dedicated liquid having the composition different from that of the measurement solution.

What is claimed is:

1. A method of detecting a test substance contained in a sample using a working electrode and a counter electrode, the method comprising:
   (A) forming a immuno-complex on the working electrode, the complex comprising the test substance and a metal particle on which an antibody to the test substance is immobilized;
   (B) washing the working electrode;
   (C) adding a measurement solution to the working electrode and measuring a current, voltage or electric charge from the metal on the working electrode in the measurement solution by electrochemical measurement; and
   (D) detecting the test substance in the sample based on a measurement result obtained in the step (C), wherein
      the step (B) comprises washing the working electrode using a measurement solution having the same composition as the composition of the measurement solution used in the step (C), and
      pH of the measurement solution is set, based on zeta potentials of the metal particle and the working electrode, to
   pH in which no electrostatic interaction occurs between the metal particle and the working electrode or
   pH in which an electrostatic repulsive force occurs between the metal particle and the working electrode, wherein, in the step (C),
      the metal due to the metal particle gathered on the working electrode is deposited on the surface of the working electrode,
      the deposited metal are subjected to a redox reaction, and
      the current, voltage or charge induced by the redox reaction is measured.

2. The method according to claim 1, wherein the pH of the measurement solution is a pH in which the zeta potential of the metal particle and the zeta potential of the working electrode have the same sign potential.

3. The method according to claim 1, wherein the measurement solution has a pH of 3.5 or more.

4. The method according to claim 1, wherein the measurement solution has a pH of 11 or less.

5. The method according to claim 1, wherein the measurement solution comprises an electrolyte.

6. The method according to claim 1, wherein the working electrode comprises carbon.

7. The method according to claim 1, wherein the metal particle is made of at least one metal selected from the group consisting of gold, silver, copper, platinum, and indium.

8. The method according to claim 1, wherein the electrochemical measurement is a method selected from the group consisting of differential pulse voltammetry, cyclic voltammetry, and chronoamperometry methods.

9. The method according to claim 1, wherein the step (B) comprises
   adding the measurement solution to the working electrode and removing the measurement solution to remove an impurity.

10. A method of detecting a test substance contained in a sample using a working electrode and a counter electrode, the method comprising:
    (A) forming a immuno-complex on the working electrode, the complex comprising the test substance and a metal particle on which an antibody to the test substance is immobilized;
    (B) washing the working electrode;
    (C) adding a measurement solution to the working electrode and measuring a current, voltage or electric charge from the metal on the working electrode in the measurement solution by electrochemical measurement; and
    (D) detecting the test substance in the sample based on a measurement result obtained in the step (C), wherein
       the step (B) comprises washing the working electrode using a measurement solution having the same composition as the composition of the measurement solution used in the step (C), and
       the measurement solution has a pH of 3.5 or more, wherein, in the step (C),
       the metal due to the metal particle gathered on the working electrode is deposited on the surface of the working electrode,
       the deposited metal are subjected to a redox reaction, and
       the current, voltage or charge induced by the redox reaction is measured.

11. The method according to claim 10, wherein the measurement solution has a pH of 11 or less.

12. The method according to claim 10, wherein the measurement solution comprises an electrolyte.

13. The method according to claim 10, wherein the working electrode comprises carbon.

14. The method according to claim 10, wherein the metal particle is made of at least one metal selected from the group consisting of gold, silver, copper, platinum, and indium.

15. The method according to claim 10, wherein the electrochemical measurement is a method selected from the group consisting of differential pulse voltammetry, cyclic voltammetry, and chronoamperometry methods.

16. The method according to claim 10, wherein the step (B) comprises
    adding the measurement solution to the working electrode and removing the measurement solution to remove an impurity.

17. A method of detecting a test substance contained in a sample using a working electrode and a counter electrode, the method comprising:
    (A) forming a immuno-complex on the working electrode, the complex comprising the test substance and a metal particle on which an antibody to the test substance is immobilized;
    (B) adding a measurement solution to the working electrode and removing the measurement solution to remove an impurity;
    (C) adding a measurement solution to the working electrode and measuring a current, voltage or electric charge from the metal on the working electrode in the measurement solution by electrochemical measurement; and
    (D) detecting the test substance in the sample based on a measurement result obtained in the step (C), wherein
       the measurement solution used in the step (B) has the same composition as the composition of the measurement solution used in the step (C),
       the measurement solution has a pH of 3.5 or more,
       the working electrode comprises carbon,
    wherein, in the step (C),
       the metal due to the metal particle gathered on the working electrode is deposited on the surface of the working electrode,
       the deposited metal are subjected to a redox reaction, and the current, voltage or charge induced by the redox reaction is measured.

* * * * *